(12) United States Patent
Mok et al.

(10) Patent No.: US 6,600,091 B1
(45) Date of Patent: Jul. 29, 2003

(54) ENZYMES RESPONSIBLE FOR THE METABOLISM OF ZEATIN

(75) Inventors: David W. S. Mok, Corvallis, OR (US); Machteld C. Mok, Corvallis, OR (US); Ruth C. Martin, Corvallis, OR (US)

(73) Assignee: The State of Oregon acting by and through the State Board of Higher Education on behalf of Oregon State University, Corvallis, OR (US)

( * ) Notice: Subject to any disclaimer, the term of this patent is extended or adjusted under 35 U.S.C. 154(b) by 0 days.

(21) Appl. No.: 09/679,263

(22) Filed: Oct. 4, 2000

Related U.S. Application Data

(63) Continuation of application No. PCT/US98/27759, filed on Dec. 24, 1998.
(60) Provisional application No. 60/080,852, filed on Apr. 6, 1998.

(51) Int. Cl.$^7$ .......................... A01H 5/00; C12N 15/29; C12N 15/52; C12N 15/82
(52) U.S. Cl. ................. 800/298; 800/298; 536/23.2; 536/23.6; 435/320.1
(58) Field of Search ......................... 536/2, 23.2, 23.6; 435/69.1, 320.1, 419; 800/285, 286, 278, 284, 298

(56) References Cited

FOREIGN PATENT DOCUMENTS

| | | | | |
|---|---|---|---|---|
| JP | 9-056385 A | * | 3/1997 | |
| JP | 09056385 A | * | 3/1997 | ........... C12N/15/09 |

OTHER PUBLICATIONS

Wolfe et al. The Effect of Relaxed Functional Constraints on the Photosynthetic Gene rbcL in Photosynthetic and Non-photosynthetic Parasitic Plants, 1998. Society for Molecular Biology and Evolution. ISSN: 0737–4038.*
Cong et al. Covalent Catalysis in Nucleotidy; Transfer 1993. vol. 268, No. 10, pp. 7256–7260.*
Gobbins et al. Genetic Manipulation of Condensed Tannins in Higher Plants, 1998. Plant Physiol, 116: 1133–1144.*
Krol et al. Inhibition of flower pigmentation by antisense CHS genes: promoter and minimal sequence requirements for the antisense effect, 1990. Plant Molecular Biology 14: 457–466.*
Crete' et al. Expression and sequence requirements for nitrite reductase co–suppression, 1999. Plant Molecular Biology 41: 105–114.*
Faske, et al. Transgenic Tobacco Plants Expressing Pea Chloroplast Nmdh cDNA in sense and Antisense Orientation, 1997. Plant Physiol, 115: 705–715.*
Wolfe, A. D. et al. Mol. Biol. Evol., 1998, 15(10):1243–1258.*
Cong et al. 1993, J. of Biol. Chemistry, vol. 286, No. 10 pp. 7256–7260.*
Robbins et al. Plant Physiol., 1998, 116: 1133–1144.*
Crete et al. Plant Mol Biol, Sep. 1999; 41(1):105–14.*
Faske et al., Plant Physiol., 1997, 115: 705–715.*
Martin et al., "Isolation of a cytokinin gene, ZOG1, encoding zeatin O–glucosyltransferase from *Phaseolus lunatus,*" *Proc. Natl. Acad. Sci. USA* 96:284–289, Jan. 1999.
Miller et al., *J. American Chem. Soc.* 77:1392, 1955.
Miller et al., *J. American Chem. Soc.* 78:1375–1380, 1956.
Letham, *Life Sci.* 8:569–573, 1963.
Shaw et al., *Proc. Chem. Soc.*, Jul. 1964, p. 231.
Mok et al. (eds.), *Cytokinins and Plant Development—An overview. In: Cytokinins, Chemistry, Activity, and Functions,* Mok et al. (eds.), CRC Press, Inc., Boca Raton, FL, 1994.
Jameson, *Cytokinin Metabolism and Compartmentation. In: Cytokinins, Chemistry, Activity and Function,* Mok et al. (eds.), CRC Press, Inc., pp. 113–128, 1994.
Letham et al., *Ann. Botany* 41:261–263, 1976.
Dixon et al., *Plant Physiol.* 90:1316–1321, 1989.
Martin et al., *Plant Physiol.* 94:1290–1294, 1990.
Hovarth et al., *Plant Mol. Biol.* 31:1061–1072, 1996.

* cited by examiner

Primary Examiner—Amy J. Nelson
Assistant Examiner—Russell Kallis
(74) Attorney, Agent, or Firm—Klarquist Sparkman, LLP

(57) ABSTRACT

Isolated nucleic acids encoding zeatin O-glucosyltransferase are disclosed. These nucleic acid molecules are useful, among other things, to produce transgenic plants having modified zeatin O-glucosyltransferase activity.

11 Claims, 3 Drawing Sheets trans-zeatin → O-glucosylzeatin

Lane 1: Native enzyme
Lane 2: Recombinant protein
Lane 3: MW markers

SEQUENCE LISTING

```
<160> NUMBER OF SEQ ID NOS:   16

<210> SEQ ID NO 1
<211> LENGTH: 1523
<212> TYPE: DNA
<213> ORGANISM: Phaseolus lunatus
<220> FEATURE:
<221> NAME/KEY: CDS
<222> LOCATION: (33)..(1409)

<400> SEQUENCE: 1
gaagcatagc atcttgctac ccaaattcac ca atg gct ttg aat gac aaa agc         53
                                    Met Ala Leu Asn Asp Lys Ser
                                     1               5 att cct cat gaa acc aaa gtg gtg gtg ctt ttg ata cct ttc cct gca        101
Ile Pro His Glu Thr Lys Val Val Val Leu Leu Ile Pro Phe Pro Ala
         10                  15                  20 caa ggt cac ctc aac cag ttt ctg cac cta tct cgc tta atc gtg gca        149
Gln Gly His Leu Asn Gln Phe Leu His Leu Ser Arg Leu Ile Val Ala
     25                  30                  35 caa aac ata cca gtc cat tat gtt ggc act gtc aca cac att cgc cag        197
Gln Asn Ile Pro Val His Tyr Val Gly Thr Val Thr His Ile Arg Gln
 40                  45                  50                  55 gca aca ctt cga tac aac aac cct act tca aac atc cat ttc cat gcc        245
Ala Thr Leu Arg Tyr Asn Asn Pro Thr Ser Asn Ile His Phe His Ala
                 60                  65                  70 ttt caa gtt cca ccc ttt gtt tcc cct cct ccc aat cca gaa gac gat        293
Phe Gln Val Pro Pro Phe Val Ser Pro Pro Pro Asn Pro Glu Asp Asp
             75                  80                  85 ttc cca tct cat cta att cct tcc ttt gag gcc tct gca cac ctt cgg        341
Phe Pro Ser His Leu Ile Pro Ser Phe Glu Ala Ser Ala His Leu Arg
         90                  95                 100 gag ccc gtg ggg aaa ctt ctt caa tcc ctc tca tca caa gcc aaa agg        389
Glu Pro Val Gly Lys Leu Leu Gln Ser Leu Ser Ser Gln Ala Lys Arg
    105                 110                 115
```

-continued

| | |
|---|---|
| gtc gta gtc atc aat gac tcc ctc atg gca tct gtg gca caa gat gcc<br>Val Val Val Ile Asn Asp Ser Leu Met Ala Ser Val Ala Gln Asp Ala<br>120                   125                   130                   135 | 437 |
| gca aac atc tca aat gtt gaa aac tac act ttt cac agc ttc tct gcc<br>Ala Asn Ile Ser Asn Val Glu Asn Tyr Thr Phe His Ser Phe Ser Ala<br>               140                   145                   150 | 485 |
| ttt aat acc tcc ggt gat ttt tgg gaa gaa atg gga aag ccc ccg gtt<br>Phe Asn Thr Ser Gly Asp Phe Trp Glu Glu Met Gly Lys Pro Pro Val<br>         155                   160                   165 | 533 |
| gga gat ttc cat ttc cca gaa ttt cct tct ctt gaa gga tgc atc gca<br>Gly Asp Phe His Phe Pro Glu Phe Pro Ser Leu Glu Gly Cys Ile Ala<br>               170                   175                   180 | 581 |
| gcc cag ttc aag ggc ttt cgt act gca cag tat gaa ttc cgc aaa ttc<br>Ala Gln Phe Lys Gly Phe Arg Thr Ala Gln Tyr Glu Phe Arg Lys Phe<br>185                   190                   195 | 629 |
| aac aat ggc gat att tac aac acc agc agg gtg att gaa ggt cct tac<br>Asn Asn Gly Asp Ile Tyr Asn Thr Ser Arg Val Ile Glu Gly Pro Tyr<br>200                   205                   210                   215 | 677 |
| gtt gag ttg ctg gag ctt ttc aat ggc ggc aag aag gtt tgg gca ttg<br>Val Glu Leu Leu Glu Leu Phe Asn Gly Gly Lys Lys Val Trp Ala Leu<br>               220                   225                   230 | 725 |
| ggg cca ttt aac cct tta gcc gtt gag aag aaa gat tca ata gga ttt<br>Gly Pro Phe Asn Pro Leu Ala Val Glu Lys Lys Asp Ser Ile Gly Phe<br>         235                   240                   245 | 773 |
| agg cac cca tgc atg gag tgg ctt gat aaa caa gag cca agt tca gtc<br>Arg His Pro Cys Met Glu Trp Leu Asp Lys Gln Glu Pro Ser Ser Val<br>               250                   255                   260 | 821 |
| ata tat ata tcc ttc ggg acc acg aca gct ttg aga gat gaa caa atc<br>Ile Tyr Ile Ser Phe Gly Thr Thr Thr Ala Leu Arg Asp Glu Gln Ile<br>265                   270                   275 | 869 |
| caa cag ata gca act ggg ttg gaa caa agc aag cag aag ttc atc tgg<br>Gln Gln Ile Ala Thr Gly Leu Glu Gln Ser Lys Gln Lys Phe Ile Trp<br>280                   285                   290                   295 | 917 |
| gtg ctg aga gaa gcc gat aaa ggg gac atc ttt gcc gga agt gaa gca<br>Val Leu Arg Glu Ala Asp Lys Gly Asp Ile Phe Ala Gly Ser Glu Ala<br>               300                   305                   310 | 965 |
| aaa agg tat gaa ctt cca aag ggt ttt gag gag aga gtg gaa gga atg<br>Lys Arg Tyr Glu Leu Pro Lys Gly Phe Glu Glu Arg Val Glu Gly Met<br>         315                   320                   325 | 1013 |
| ggg ctg gtt gtg agg gac tgg gca ccc caa ttg gaa att ctg agc cac<br>Gly Leu Val Val Arg Asp Trp Ala Pro Gln Leu Glu Ile Leu Ser His<br>               330                   335                   340 | 1061 |
| agt tca aca ggg ggg ttt atg agc cat tgt gga tgg aac tcg tgc ttg<br>Ser Ser Thr Gly Gly Phe Met Ser His Cys Gly Trp Asn Ser Cys Leu<br>         345                   350                   355 | 1109 |
| gag agc ata acc atg ggg gtg cca ata gca aca tgg ccc atg cac tct<br>Glu Ser Ile Thr Met Gly Val Pro Ile Ala Thr Trp Pro Met His Ser<br>360                   365                   370                   375 | 1157 |
| gac cag cca aga aat gca gtt ttg gtt aca gag gtt ctg aag gtt ggt<br>Asp Gln Pro Arg Asn Ala Val Leu Val Thr Glu Val Leu Lys Val Gly<br>               380                   385                   390 | 1205 |
| ttg gtt gtg aag gat tgg gca cag agg aat tcg ttg gtg agt gct tca<br>Leu Val Val Lys Asp Trp Ala Gln Arg Asn Ser Leu Val Ser Ala Ser<br>         395                   400                   405 | 1253 |
| gtt gtt gag aat ggt gtg aga agg ttg atg gaa aca aag gaa ggt gat<br>Val Val Glu Asn Gly Val Arg Arg Leu Met Glu Thr Lys Glu Gly Asp<br>               410                   415                   420 | 1301 |
| gag atg aga cag aga gca gtg agg ctt aaa aat gcc atc cat agg tca<br>Glu Met Arg Gln Arg Ala Val Arg Leu Lys Asn Ala Ile His Arg Ser<br>425                   430                   435 | 1349 |

-continued

```
atg gat gaa ggt gga gtt tct cac atg gag atg ggt tct ttc att gca    1397
Met Asp Glu Gly Gly Val Ser His Met Glu Met Gly Ser Phe Ile Ala
440                 445                 450                 455 cac atc tct aaa tagtcatacc atttagcctg ttcttatagc aaaatatgac        1449
His Ile Ser Lys agaagttagt tgtcatcatg ttgttgatgc aaaataattt cctatgacat tatccaataa  1509
taaagcttct gttg                                                    1523

<210> SEQ ID NO 2
<211> LENGTH: 1632
<212> TYPE: DNA
<213> ORGANISM: Phaseolus lunatus
<220> FEATURE:
<221> NAME/KEY: CDS
<222> LOCATION: (142)..(1518)

<400> SEQUENCE: 2
aagcttttaa ataagaaata tttttttgcta tatataaatc ttgagtataa aatgtatgtt    60
catacttgat ctactaccaa cttaagcata agcagccagt gtcaaagttg aagcatagca   120
tcttgctacc caaattcacc a atg gct ttg aat gac aaa agc att cct cat      171
                        Met Ala Leu Asn Asp Lys Ser Ile Pro His
                         1               5                  10 gaa acc aaa gtg gtg gtg ctt ttg ata cct ttc cct gca caa ggt cac     219
Glu Thr Lys Val Val Val Leu Leu Ile Pro Phe Pro Ala Gln Gly His
                15                  20                  25 ctc aac cag ttt ctg cac cta tct cgc tta atc gtg gca caa aac ata    267
Leu Asn Gln Phe Leu His Leu Ser Arg Leu Ile Val Ala Gln Asn Ile
             30                  35                  40 cca gtc cat tat gtt ggc act gtc aca cac att cgc cag gca aca ctt    315
Pro Val His Tyr Val Gly Thr Val Thr His Ile Arg Gln Ala Thr Leu
         45                  50                  55 cga tac aac aac cct act tca aac atc cat ttc cat gcc ttt caa gtt    363
Arg Tyr Asn Asn Pro Thr Ser Asn Ile His Phe His Ala Phe Gln Val
     60                  65                  70 cca ccc ttt gtt tcc cct cct ccc aat cca gaa gac gat ttc cca tct    411
Pro Pro Phe Val Ser Pro Pro Pro Asn Pro Glu Asp Asp Phe Pro Ser
 75                  80                  85                  90 cat cta att cct tcc ttt gag gcc tct gca cac ctt cgg gag ccc gtg    459
His Leu Ile Pro Ser Phe Glu Ala Ser Ala His Leu Arg Glu Pro Val
                 95                 100                 105 ggg aaa ctt ctt caa tcc ctc tca tca caa gcc aaa agg gtc gta gtc    507
Gly Lys Leu Leu Gln Ser Leu Ser Ser Gln Ala Lys Arg Val Val Val
            110                 115                 120 atc aat gac tcc ctc atg gca tct gtg gca caa gat gcc gca aac atc    555
Ile Asn Asp Ser Leu Met Ala Ser Val Ala Gln Asp Ala Ala Asn Ile
        125                 130                 135 tca aat gtt gaa aac tac act ttt cac agc ttc tct gcc ttt aat acc    603
Ser Asn Val Glu Asn Tyr Thr Phe His Ser Phe Ser Ala Phe Asn Thr
    140                 145                 150 tcc ggt gat ttt tgg gaa gaa atg gga aag ccc ccg gtt gga gat ttc    651
Ser Gly Asp Phe Trp Glu Glu Met Gly Lys Pro Pro Val Gly Asp Phe
155                 160                 165                 170 cat ttc cca gaa ttt cct tct ctt gaa gga tgc atc gca gcc cag ttc    699
His Phe Pro Glu Phe Pro Ser Leu Glu Gly Cys Ile Ala Ala Gln Phe
                175                 180                 185 aag ggc ttt cgt act gca cag tat gaa ttc cgc aaa ttc aac aat ggc    747
Lys Gly Phe Arg Thr Ala Gln Tyr Glu Phe Arg Lys Phe Asn Asn Gly
            190                 195                 200
```

```
gat att tac aac acc agc agg gtg att gaa ggt cct tac gtt gag ttg      795
Asp Ile Tyr Asn Thr Ser Arg Val Ile Glu Gly Pro Tyr Val Glu Leu
        205                 210                 215 ctg gag ctt ttc aat ggc ggc aag aag gtt tgg gca ttg ggg cca ttt      843
Leu Glu Leu Phe Asn Gly Gly Lys Lys Val Trp Ala Leu Gly Pro Phe
    220                 225                 230 aac cct tta gcc gtt gag aag aaa gat tca ata gga ttt agg cac cca      891
Asn Pro Leu Ala Val Glu Lys Lys Asp Ser Ile Gly Phe Arg His Pro
235                 240                 245                 250 tgc atg gag tgg ctt gat aaa caa gag cca agt tca gtc ata tat ata      939
Cys Met Glu Trp Leu Asp Lys Gln Glu Pro Ser Ser Val Ile Tyr Ile
                255                 260                 265 tcc ttc ggg acc acg aca gct ttg aga gat gaa caa atc caa cag ata      987
Ser Phe Gly Thr Thr Thr Ala Leu Arg Asp Glu Gln Ile Gln Gln Ile
        270                 275                 280 gca act ggg ttg gaa caa agc aag cag aag ttc atc tgg gtg ctg aga     1035
Ala Thr Gly Leu Glu Gln Ser Lys Gln Lys Phe Ile Trp Val Leu Arg
    285                 290                 295 gaa gcc gat aaa ggg gac atc ttt gcc gga agt gaa gca aaa agg tat     1083
Glu Ala Asp Lys Gly Asp Ile Phe Ala Gly Ser Glu Ala Lys Arg Tyr
300                 305                 310 gaa ctt cca aag ggt ttt gag gag aga gtg gaa gga atg ggg ctg gtt     1131
Glu Leu Pro Lys Gly Phe Glu Glu Arg Val Glu Gly Met Gly Leu Val
315                 320                 325                 330 gtg agg gac tgg gca ccc caa ttg gaa att ctg agc cac agt tca aca     1179
Val Arg Asp Trp Ala Pro Gln Leu Glu Ile Leu Ser His Ser Ser Thr
                335                 340                 345 ggg ggg ttt atg agc cat tgt gga tgg aac tcg tgc ttg gag agc ata     1227
Gly Gly Phe Met Ser His Cys Gly Trp Asn Ser Cys Leu Glu Ser Ile
        350                 355                 360 acc atg ggg gtg cca ata gca aca tgg ccc atg cac tct gac cag cca     1275
Thr Met Gly Val Pro Ile Ala Thr Trp Pro Met His Ser Asp Gln Pro
    365                 370                 375 aga aat gca gtt ttg gtt aca gag gtt ctg aag gtt ggt ttg gtt gtg     1323
Arg Asn Ala Val Leu Val Thr Glu Val Leu Lys Val Gly Leu Val Val
380                 385                 390 aag gat tgg gca cag agg aat tcg ttg gtg agt gct tca gtt gtt gag     1371
Lys Asp Trp Ala Gln Arg Asn Ser Leu Val Ser Ala Ser Val Val Glu
395                 400                 405                 410 aat ggt gtg aga agg ttg atg gaa aca aag gaa ggt gat gag atg aga     1419
Asn Gly Val Arg Arg Leu Met Glu Thr Lys Glu Gly Asp Glu Met Arg
                415                 420                 425 cag aga gca gtg agg ctt aaa aat gcc atc cat agg tca atg gat gaa     1467
Gln Arg Ala Val Arg Leu Lys Asn Ala Ile His Arg Ser Met Asp Glu
        430                 435                 440 ggt gga gtt tct cac atg gag atg ggt tct ttc att gca cac atc tct     1515
Gly Gly Val Ser His Met Glu Met Gly Ser Phe Ile Ala His Ile Ser
    445                 450                 455 aaa                                                                 1518
Lys tagtcatacc atttagcctg ttcttatagc aaaatatgac agaagttagt               1568
tgtcatcatg ttgttgatgc aaaataattt cctatgacat tatccaataa taaagcttct   1628
gttg                                                                1632

<210> SEQ ID NO 3
<211> LENGTH: 1377
<212> TYPE: DNA
<213> ORGANISM: Phaseolus lunatus
<220> FEATURE:
<221> NAME/KEY: CDS
<222> LOCATION: (1)..(1377)
```

-continued

<400> SEQUENCE: 3

| | | |
|---|---|---|
| atg gct ttg aat gac aaa agc att cct cat gaa acc aaa gtg gtg gtg<br>Met Ala Leu Asn Asp Lys Ser Ile Pro His Glu Thr Lys Val Val Val<br>1               5                   10                  15 | 48 |
| ctt ttg ata cct ttc cct gca caa ggt cac ctc aac cag ttt ctg cac<br>Leu Leu Ile Pro Phe Pro Ala Gln Gly His Leu Asn Gln Phe Leu His<br>            20                  25                  30 | 96 |
| cta tct cgc tta atc gtg gca caa aac ata cca gtc cat tat gtt ggc<br>Leu Ser Arg Leu Ile Val Ala Gln Asn Ile Pro Val His Tyr Val Gly<br>        35                  40                  45 | 144 |
| act gtc aca cac att cgc cag gca aca ctt cga tac aac aac cct act<br>Thr Val Thr His Ile Arg Gln Ala Thr Leu Arg Tyr Asn Asn Pro Thr<br>    50                  55                  60 | 192 |
| tca aac atc cat ttc cat gcc ttt caa gtt cca ccc ttt gtt tcc cct<br>Ser Asn Ile His Phe His Ala Phe Gln Val Pro Pro Phe Val Ser Pro<br>65                  70                  75                  80 | 240 |
| cct ccc aat cca gaa gac gat ttc cca tct cat cta att cct tcc ttt<br>Pro Pro Asn Pro Glu Asp Asp Phe Pro Ser His Leu Ile Pro Ser Phe<br>                85                  90                  95 | 288 |
| gag gcc tct gca cac ctt cgg gag ccc gtg ggg aaa ctt ctt caa tcc<br>Glu Ala Ser Ala His Leu Arg Glu Pro Val Gly Lys Leu Leu Gln Ser<br>            100                 105                 110 | 336 |
| ctc tca tca caa gcc aaa agg gtc gta gtc atc aat gac tcc ctc atg<br>Leu Ser Ser Gln Ala Lys Arg Val Val Val Ile Asn Asp Ser Leu Met<br>        115                 120                 125 | 384 |
| gca tct gtg gca caa gat gcc gca aac atc tca aat gtt gaa aac tac<br>Ala Ser Val Ala Gln Asp Ala Ala Asn Ile Ser Asn Val Glu Asn Tyr<br>    130                 135                 140 | 432 |
| act ttt cac agc ttc tct gcc ttt aat acc tcc ggt gat ttt tgg gaa<br>Thr Phe His Ser Phe Ser Ala Phe Asn Thr Ser Gly Asp Phe Trp Glu<br>145                 150                 155                 160 | 480 |
| gaa atg gga aag ccc ccg gtt gga gat ttc cat ttc cca gaa ttt cct<br>Glu Met Gly Lys Pro Pro Val Gly Asp Phe His Phe Pro Glu Phe Pro<br>                165                 170                 175 | 528 |
| tct ctt gaa gga tgc atc gca gcc cag ttc aag ggc ttt cgt act gca<br>Ser Leu Glu Gly Cys Ile Ala Ala Gln Phe Lys Gly Phe Arg Thr Ala<br>            180                 185                 190 | 576 |
| cag tat gaa ttc cgc aaa ttc aac aat ggc gat att tac aac acc agc<br>Gln Tyr Glu Phe Arg Lys Phe Asn Asn Gly Asp Ile Tyr Asn Thr Ser<br>        195                 200                 205 | 624 |
| agg gtg att gaa ggt cct tac gtt gag ttg ctg gag ctt ttc aat ggc<br>Arg Val Ile Glu Gly Pro Tyr Val Glu Leu Leu Glu Leu Phe Asn Gly<br>    210                 215                 220 | 672 |
| ggc aag aag gtt tgg gca ttg ggg cca ttt aac cct tta gcc gtt gag<br>Gly Lys Lys Val Trp Ala Leu Gly Pro Phe Asn Pro Leu Ala Val Glu<br>225                 230                 235                 240 | 720 |
| aag aaa gat tca ata gga ttt agg cac cca tgc atg gag tgg ctt gat<br>Lys Lys Asp Ser Ile Gly Phe Arg His Pro Cys Met Glu Trp Leu Asp<br>                245                 250                 255 | 768 |
| aaa caa gag cca agt tca gtc ata tat ata tcc ttc ggg acc acg aca<br>Lys Gln Glu Pro Ser Ser Val Ile Tyr Ile Ser Phe Gly Thr Thr Thr<br>            260                 265                 270 | 816 |
| gct ttg aga gat gaa caa atc caa cag ata gca act ggg ttg gaa caa<br>Ala Leu Arg Asp Glu Gln Ile Gln Gln Ile Ala Thr Gly Leu Glu Gln<br>        275                 280                 285 | 864 |
| agc aag cag aag ttc atc tgg gtg ctg aga gaa gcc gat aaa ggg gac<br>Ser Lys Gln Lys Phe Ile Trp Val Leu Arg Glu Ala Asp Lys Gly Asp<br>    290                 295                 300 | 912 |

-continued

```
atc ttt gcc gga agt gaa gca aaa agg tat gaa ctt cca aag ggt ttt      960
Ile Phe Ala Gly Ser Glu Ala Lys Arg Tyr Glu Leu Pro Lys Gly Phe
305                 310                 315                 320 gag gag aga gtg gaa gga atg ggg ctg gtt gtg agg gac tgg gca ccc     1008
Glu Glu Arg Val Glu Gly Met Gly Leu Val Val Arg Asp Trp Ala Pro
                325                 330                 335 caa ttg gaa att ctg agc cac agt tca aca ggg ggg ttt atg agc cat     1056
Gln Leu Glu Ile Leu Ser His Ser Ser Thr Gly Gly Phe Met Ser His
            340                 345                 350 tgt gga tgg aac tcg tgc ttg gag agc ata acc atg ggg gtg cca ata     1104
Cys Gly Trp Asn Ser Cys Leu Glu Ser Ile Thr Met Gly Val Pro Ile
        355                 360                 365 gca aca tgg ccc atg cac tct gac cag cca aga aat gca gtt ttg gtt     1152
Ala Thr Trp Pro Met His Ser Asp Gln Pro Arg Asn Ala Val Leu Val
    370                 375                 380 aca gag gtt ctg aag gtt ggt ttg gtt gtg aag gat tgg gca cag agg     1200
Thr Glu Val Leu Lys Val Gly Leu Val Val Lys Asp Trp Ala Gln Arg
385                 390                 395                 400 aat tcg ttg gtg agt gct tca gtt gtt gag aat ggt gtg aga agg ttg     1248
Asn Ser Leu Val Ser Ala Ser Val Val Glu Asn Gly Val Arg Arg Leu
                405                 410                 415 atg gaa aca aag gaa ggt gat gag atg aga cag aga gca gtg agg ctt     1296
Met Glu Thr Lys Glu Gly Asp Glu Met Arg Gln Arg Ala Val Arg Leu
            420                 425                 430 aaa aat gcc atc cat agg tca atg gat gaa ggt gga gtt tct cac atg     1344
Lys Asn Ala Ile His Arg Ser Met Asp Glu Gly Gly Val Ser His Met
        435                 440                 445 gag atg ggt tct ttc att gca cac atc tct aaa                          1377
Glu Met Gly Ser Phe Ile Ala His Ile Ser Lys
    450                 455
```

<210> SEQ ID NO 4
<211> LENGTH: 459
<212> TYPE: PRT
<213> ORGANISM: Phaseolus lunatus

<400> SEQUENCE: 4

```
Met Ala Leu Asn Asp Lys Ser Ile Pro His Glu Thr Lys Val Val Val
  1               5                  10                  15

Leu Leu Ile Pro Phe Pro Ala Gln Gly His Leu Asn Gln Phe Leu His
             20                  25                  30

Leu Ser Arg Leu Ile Val Ala Gln Asn Ile Pro Val His Tyr Val Gly
         35                  40                  45

Thr Val Thr His Ile Arg Gln Ala Thr Leu Arg Tyr Asn Asn Pro Thr
     50                  55                  60

Ser Asn Ile His Phe His Ala Phe Gln Val Pro Phe Val Ser Pro
 65                  70                  75                  80

Pro Pro Asn Pro Glu Asp Asp Phe Pro Ser His Leu Ile Pro Ser Phe
                 85                  90                  95

Glu Ala Ser Ala His Leu Arg Glu Pro Val Gly Lys Leu Leu Gln Ser
            100                 105                 110

Leu Ser Ser Gln Ala Lys Arg Val Val Val Ile Asn Asp Ser Leu Met
        115                 120                 125

Ala Ser Val Ala Gln Asp Ala Ala Asn Ile Ser Asn Val Glu Asn Tyr
    130                 135                 140

Thr Phe His Ser Phe Ser Ala Phe Asn Thr Ser Gly Asp Phe Trp Glu
145                 150                 155                 160

Glu Met Gly Lys Pro Pro Val Gly Asp Phe His Glu Pro Glu Phe Pro
```

```
                165                 170                 175
Ser Leu Glu Gly Cys Ile Ala Ala Gln Phe Lys Gly Phe Arg Thr Ala
                180                 185                 190
Gln Tyr Glu Phe Arg Lys Phe Asn Asn Gly Asp Ile Tyr Asn Thr Ser
                195                 200                 205
Arg Val Ile Glu Gly Pro Tyr Val Glu Leu Glu Leu Phe Asn Gly
210                 215                 220
Gly Lys Lys Val Trp Ala Leu Gly Pro Phe Asn Pro Leu Ala Val Glu
225                 230                 235                 240
Lys Lys Asp Ser Ile Gly Phe Arg His Pro Cys Met Glu Trp Leu Asp
                245                 250                 255
Lys Gln Glu Pro Ser Ser Val Ile Tyr Ile Ser Phe Gly Thr Thr Thr
                260                 265                 270
Ala Leu Arg Asp Glu Gln Ile Gln Gln Ile Ala Thr Gly Leu Glu Gln
                275                 280                 285
Ser Lys Gln Lys Phe Ile Trp Val Leu Arg Glu Ala Asp Lys Gly Asp
                290                 295                 300
Ile Phe Ala Gly Ser Glu Ala Lys Arg Tyr Glu Leu Pro Lys Gly Phe
305                 310                 315                 320
Glu Glu Arg Val Glu Gly Met Gly Leu Val Val Arg Asp Trp Ala Pro
                325                 330                 335
Gln Leu Glu Ile Leu Ser His Ser Ser Thr Gly Gly Phe Met Ser His
                340                 345                 350
Cys Gly Trp Asn Ser Cys Leu Glu Ser Ile Thr Met Gly Val Pro Ile
                355                 360                 365
Ala Thr Trp Pro Met His Ser Asp Gln Pro Arg Asn Ala Val Leu Val
                370                 375                 380
Thr Glu Val Leu Lys Val Gly Leu Val Val Lys Asp Trp Ala Gln Arg
385                 390                 395                 400
Asn Ser Leu Val Ser Ala Ser Val Val Glu Asn Gly Val Arg Arg Leu
                405                 410                 415
Met Glu Thr Lys Glu Gly Asp Glu Met Arg Gln Arg Ala Val Arg Leu
                420                 425                 430
Lys Asn Ala Ile His Arg Ser Met Asp Glu Gly Gly Val Ser His Met
                435                 440                 445
Glu Met Gly Ser Phe Ile Ala His Ile Ser Lys
                450                 455

<210> SEQ ID NO 5
<211> LENGTH: 503
<212> TYPE: PRT
<213> ORGANISM: Phaseolus lunatus

<400> SEQUENCE: 5

Met Thr Met Ile Thr Pro Ser Ser Asn Thr Thr His Tyr Arg Glu Ser
1               5                   10                  15
Trp Tyr Ala Cys Arg Tyr Arg Ser Gly Ile Pro Gly Ser Thr His Ala
                20                  25                  30
Ser Gly Ser Ile Ala Ser Cys Tyr Pro Asn Ser Pro Met Ala Leu Asn
            35                  40                  45
Asp Lys Ser Ile Pro His Glu Thr Lys Val Val Leu Leu Ile Pro
    50                  55                  60
Phe Pro Ala Gln Gly His Leu Asn Gln Phe Leu His Leu Ser Arg Leu
65                  70                  75                  80
```

-continued

```
Ile Val Ala Gln Asn Ile Pro Val His Tyr Val Gly Thr Val Thr His
                85                  90                  95

Ile Arg Gln Ala Thr Leu Arg Tyr Asn Asn Pro Thr Ser Asn Ile His
            100                 105                 110

Phe His Ala Phe Gln Val Pro Pro Phe Val Ser Pro Pro Asn Pro
            115                 120             125

Glu Asp Asp Phe Pro Ser His Leu Ile Pro Ser Phe Glu Ala Ser Ala
    130                 135                 140

His Leu Arg Glu Pro Val Gly Lys Leu Leu Gln Ser Leu Ser Ser Gln
145                 150                 155                 160

Ala Lys Arg Val Val Ile Asn Asp Ser Leu Met Ala Ser Val Ala
                165                 170                 175

Gln Asp Ala Ala Asn Ile Ser Asn Val Glu Asn Tyr Thr Phe His Ser
            180                 185                 190

Phe Ser Ala Phe Asn Thr Ser Gly Asp Phe Trp Glu Glu Met Gly Lys
        195                 200                 205

Pro Pro Val Gly Asp Phe His Glu Pro Glu Phe Pro Ser Leu Glu Gly
    210                 215                 220

Cys Ile Ala Ala Gln Phe Lys Gly Phe Arg Thr Ala Gln Tyr Glu Phe
225                 230                 235                 240

Arg Lys Phe Asn Asn Gly Asp Ile Tyr Asn Thr Ser Arg Val Ile Glu
                245                 250                 255

Gly Pro Tyr Val Glu Leu Leu Glu Leu Phe Asn Gly Gly Lys Lys Val
            260                 265                 270

Trp Ala Leu Gly Pro Phe Asn Pro Leu Ala Val Glu Lys Lys Asp Ser
        275                 280                 285

Ile Gly Phe Arg His Pro Cys Met Glu Trp Leu Asp Lys Gln Glu Pro
    290                 295                 300

Ser Ser Val Ile Tyr Ile Ser Phe Gly Thr Thr Thr Ala Leu Arg Asp
305                 310                 315                 320

Glu Gln Ile Gln Gln Ile Ala Thr Gly Leu Glu Gln Ser Lys Gln Lys
                325                 330                 335

Phe Ile Trp Val Leu Arg Glu Ala Asp Lys Gly Asp Ile Phe Ala Gly
            340                 345                 350

Ser Glu Ala Lys Arg Tyr Glu Leu Pro Lys Gly Phe Glu Glu Arg Val
        355                 360                 365

Glu Gly Met Gly Leu Val Val Arg Asp Trp Ala Pro Gln Leu Glu Ile
    370                 375                 380

Leu Ser His Ser Ser Thr Gly Gly Phe Met Ser His Cys Gly Trp Asn
385                 390                 395                 400

Ser Cys Leu Glu Ser Ile Thr Met Gly Val Pro Ile Ala Thr Trp Pro
                405                 410                 415

Met His Ser Asp Gln Pro Arg Asn Ala Val Leu Val Thr Glu Val Leu
            420                 425                 430

Lys Val Gly Leu Val Val Lys Asp Trp Ala Gln Arg Asn Ser Leu Val
        435                 440                 445

Ser Ala Ser Val Val Glu Asn Gly Val Arg Arg Leu Met Glu Thr Lys
    450                 455                 460

Glu Gly Asp Glu Met Arg Gln Arg Ala Val Arg Leu Lys Asn Ala Ile
465                 470                 475                 480

His Arg Ser Met Asp Glu Gly Val Ser His Met Glu Met Gly Ser
                485                 490                 495

Phe Ile Ala His Ile Ser Lys
```

<210> SEQ ID NO 6
<211> LENGTH: 141
<212> TYPE: DNA
<213> ORGANISM: Phaseolus lunatus

<400> SEQUENCE: 6
aagcttttaa ataagaaata tttttgcta tatataaatc ttgagtataa aatgtatgtt      60
catacttgat ctactaccaa cttaagcata agcagccagt gtcaaagttg aagcatagca    120
tcttgctacc caaattcacc a                                              141

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:PCR Primer

<400> SEQUENCE: 7
gaagcatagc atcttgctac c                                               21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:PCR Primer

<400> SEQUENCE: 8
caacagaagc tttattattg g                                               21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:PCR Primer

<400> SEQUENCE: 9
atggctttga atgacaaaag c                                               21

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:PCR primer

<400> SEQUENCE: 10
ctatttagag atgtgtgcaa tg                                              22

<210> SEQ ID NO 11
<211> LENGTH: 1365
<212> TYPE: DNA
<213> ORGANISM: Phaseolus vulgaris
<220> FEATURE:
<221> NAME/KEY: CDS
<222> LOCATION: (1)..(1365)

<400> SEQUENCE: 11 atg gct ttg aat gat gaa acc aaa gtg gtg gtg ctt ttg cta cct ttc      48
Met Ala Leu Asn Asp Glu Thr Lys Val Val Val Leu Leu Leu Pro Phe
  1               5                  10                  15

-continued

| | |
|---|---|
| cct gta caa ggt cac ctt aac ccg ttt ctg cag cta tcc cac cta atc<br>Pro Val Gln Gly His Leu Asn Pro Phe Leu Gln Leu Ser His Leu Ile<br>           20                      25                   30 | 96 |
| gcg gca caa aac ata gca gtg cat tat gtt ggc act gtc aca cac att<br>Ala Ala Gln Asn Ile Ala Val His Tyr Val Gly Thr Val Thr His Ile<br>   35                      40                      45 | 144 |
| cgc caa gca aaa ctt cga tac cac aac gct act tca aac atc cat ttc<br>Arg Gln Ala Lys Leu Arg Tyr His Asn Ala Thr Ser Asn Ile His Phe<br>50                      55                      60 | 192 |
| cat gcc ttt gaa gtt cca ccc tat gtt tct cct cct ccc aat cca gaa<br>His Ala Phe Glu Val Pro Pro Tyr Val Ser Pro Pro Pro Asn Pro Glu<br>65                      70                     75                  80 | 240 |
| gac gat ttc cca tct cat ctc att cct tcc ttt gag gcc tct gca cac<br>Asp Asp Phe Pro Ser His Leu Ile Pro Ser Phe Glu Ala Ser Ala His<br>                 85                      90                      95 | 288 |
| ctt cgg gag cct gtg ggg aaa ctg ctt caa tcc ctt tcg tca caa gcc<br>Leu Arg Glu Pro Val Gly Lys Leu Leu Gln Ser Leu Ser Ser Gln Ala<br>           100                      105                  110 | 336 |
| aaa agg gtc gta ctc atc aat gac tcc ctc atg gca tcc gtg gca caa<br>Lys Arg Val Val Leu Ile Asn Asp Ser Leu Met Ala Ser Val Ala Gln<br>           115                      120                  125 | 384 |
| gat gct gca aac ttc tca aat gtt gaa aga tac tgt ttt caa gtc ttc<br>Asp Ala Ala Asn Phe Ser Asn Val Glu Arg Tyr Cys Phe Gln Val Phe<br>130                     135                     140 | 432 |
| tct gcc ctt aat acc gcc ggt gat ttt tgg gaa caa atg gga aag ccc<br>Ser Ala Leu Asn Thr Ala Gly Asp Phe Trp Glu Gln Met Gly Lys Pro<br>145                     150                     155                  160 | 480 |
| cct ctt gca gat ttc cat ttc cca gat att cct tct ctc caa gga tgc<br>Pro Leu Ala Asp Phe His Phe Pro Asp Ile Pro Ser Leu Gln Gly Cys<br>                       165                      170                  175 | 528 |
| atc tca gcc cag ttc acg gat ttt ctt act gca cag aat gaa ttc cgc<br>Ile Ser Ala Gln Phe Thr Asp Phe Leu Thr Ala Gln Asn Glu Phe Arg<br>           180                      185                  190 | 576 |
| aaa ttc aac aat ggc gat att tac aac acc agc agg gtg att gag ggt<br>Lys Phe Asn Asn Gly Asp Ile Tyr Asn Thr Ser Arg Val Ile Glu Gly<br>                       195                      200                  205 | 624 |
| cct tac gtt gag ttg ctg gag cgt ttc aat ggc ggc aag gag gtt tgg<br>Pro Tyr Val Glu Leu Leu Glu Arg Phe Asn Gly Gly Lys Glu Val Trp<br>210                     215                     220 | 672 |
| gca ctg ggg cca ttc acc cct tta gcc gtt gag aag aaa gat tcg ata<br>Ala Leu Gly Pro Phe Thr Pro Leu Ala Val Glu Lys Lys Asp Ser Ile<br>225                     230                     235                  240 | 720 |
| gga ttt agt cac cca tgc atg gag tgg ctt gat aaa caa gag cca agt<br>Gly Phe Ser His Pro Cys Met Glu Trp Leu Asp Lys Gln Glu Pro Ser<br>                       245                      250                  255 | 768 |
| tca gtg ata tat gta tcc ttc ggg acc acc aca gct ttg aga gat gaa<br>Ser Val Ile Tyr Val Ser Phe Gly Thr Thr Thr Ala Leu Arg Asp Glu<br>           260                      265                  270 | 816 |
| caa atc caa gag cta gca act ggg ttg gaa cag agc aag cag aag ttc<br>Gln Ile Gln Glu Leu Ala Thr Gly Leu Glu Gln Ser Lys Gln Lys Phe<br>275                     280                     285 | 864 |
| atc tgg gtg ctg aga gat gct gat aaa ggt gat atc ttt gac gga agt<br>Ile Trp Val Leu Arg Asp Ala Asp Lys Gly Asp Ile Phe Asp Gly Ser<br>           290                      295                  300 | 912 |
| gaa gca aaa agg tat gaa ctt cca gag ggt ttt gag gag aga gtg gaa<br>Glu Ala Lys Arg Tyr Glu Leu Pro Glu Gly Phe Glu Glu Arg Val Glu<br>305                     310                     315                  320 | 960 |
| gga atg ggg ctg gtt gtg agg gat tgg gca ccc caa atg gaa att ctg<br>Gly Met Gly Leu Val Val Arg Asp Trp Ala Pro Gln Met Glu Ile Leu<br>           325                      330                  335 | 1008 |

```
agc cac agt tca aca ggg ggg ttc atg agc cat tgt gga tgg aac tcg      1056
Ser His Ser Ser Thr Gly Gly Phe Met Ser His Cys Gly Trp Asn Ser
            340                 345                 350 tgc ttg gag agc tta acc agg ggg gtg cca atg gct aca tgg gcc atg      1104
Cys Leu Glu Ser Leu Thr Arg Gly Val Pro Met Ala Thr Trp Ala Met
            355                 360                 365 cac tct gac cag cca aga aat gca gtt ttg gtg aca gat gtt ctg aag      1152
His Ser Asp Gln Pro Arg Asn Ala Val Leu Val Thr Asp Val Leu Lys
        370                 375                 380 gtt ggt ttg att gtg aag gat tgg gaa cag aga aaa tcg ttg gtg agt      1200
Val Gly Leu Ile Val Lys Asp Trp Glu Gln Arg Lys Ser Leu Val Ser
385                 390                 395                 400 gct tca gtt att gag aat gct gtg aga agg ttg atg gaa aca aag gaa      1248
Ala Ser Val Ile Glu Asn Ala Val Arg Arg Leu Met Glu Thr Lys Glu
                405                 410                 415 ggt gat gag atc aga aag aga gca gtg aag ctt aaa gat gag atc cat      1296
Gly Asp Glu Ile Arg Lys Arg Ala Val Lys Leu Lys Asp Glu Ile His
            420                 425                 430 agg tcc atg gat gaa ggt gga gtt tct cgc atg gag atg gct tct ttc      1344
Arg Ser Met Asp Glu Gly Gly Val Ser Arg Met Glu Met Ala Ser Phe
            435                 440                 445 att gca cac atc tct aga tag                                          1365
Ile Ala His Ile Ser Arg
        450                 455

<210> SEQ ID NO 12
<211> LENGTH: 454
<212> TYPE: PRT
<213> ORGANISM: Phaseolus vulgaris

<400> SEQUENCE: 12

Met Ala Leu Asn Asp Glu Thr Lys Val Val Leu Leu Pro Phe
  1               5                  10                  15

Pro Val Gln Gly His Leu Asn Pro Phe Leu Gln Leu Ser His Leu Ile
                20                  25                  30

Ala Ala Gln Asn Ile Ala Val His Tyr Val Gly Thr Val Thr His Ile
            35                  40                  45

Arg Gln Ala Lys Leu Arg Tyr His Asn Ala Thr Ser Asn Ile His Phe
        50                  55                  60

His Ala Phe Glu Val Pro Pro Tyr Val Ser Pro Pro Asn Pro Glu
 65                  70                  75                  80

Asp Asp Phe Pro Ser His Leu Ile Pro Ser Phe Glu Ala Ser Ala His
                85                  90                  95

Leu Arg Glu Pro Val Gly Lys Leu Leu Gln Ser Leu Ser Ser Gln Ala
            100                 105                 110

Lys Arg Val Val Leu Ile Asn Asp Ser Leu Met Ala Ser Val Ala Gln
        115                 120                 125

Asp Ala Ala Asn Phe Ser Asn Val Glu Arg Tyr Cys Phe Gln Val Phe
    130                 135                 140

Ser Ala Leu Asn Thr Ala Gly Asp Phe Trp Gln Met Gly Lys Pro
145                 150                 155                 160

Pro Leu Ala Asp Phe His Phe Pro Asp Ile Pro Ser Leu Gln Gly Cys
                165                 170                 175

Ile Ser Ala Gln Phe Thr Asp Phe Leu Thr Ala Gln Asn Glu Phe Arg
            180                 185                 190

Lys Phe Asn Asn Gly Asp Ile Tyr Asn Thr Ser Arg Val Ile Glu Gly
        195                 200                 205
```

Pro Tyr Val Glu Leu Leu Glu Arg Phe Asn Gly Lys Glu Val Trp
    210                 215                 220

Ala Leu Gly Pro Phe Thr Pro Leu Ala Val Glu Lys Lys Asp Ser Ile
225                 230                 235                 240

Gly Phe Ser His Pro Cys Met Glu Trp Leu Asp Lys Gln Glu Pro Ser
                245                 250                 255

Ser Val Ile Tyr Val Ser Phe Gly Thr Thr Ala Leu Arg Asp Glu
            260                 265                 270

Gln Ile Gln Glu Leu Ala Thr Gly Leu Glu Gln Ser Lys Gln Lys Phe
        275                 280                 285

Ile Trp Val Leu Arg Asp Ala Asp Lys Gly Asp Ile Phe Asp Gly Ser
    290                 295                 300

Glu Ala Lys Arg Tyr Glu Leu Pro Glu Gly Phe Glu Glu Arg Val Glu
305                 310                 315                 320

Gly Met Gly Leu Val Val Arg Asp Trp Ala Pro Gln Met Glu Ile Leu
                325                 330                 335

Ser His Ser Ser Thr Gly Gly Phe Met Ser His Cys Gly Trp Asn Ser
            340                 345                 350

Cys Leu Glu Ser Leu Thr Arg Gly Val Pro Met Ala Thr Trp Ala Met
        355                 360                 365

His Ser Asp Gln Pro Arg Asn Ala Val Leu Val Thr Asp Val Leu Lys
    370                 375                 380

Val Gly Leu Ile Val Lys Asp Trp Glu Gln Arg Lys Ser Leu Val Ser
385                 390                 395                 400

Ala Ser Val Ile Glu Asn Ala Val Arg Arg Leu Met Glu Thr Lys Glu
                405                 410                 415

Gly Asp Glu Ile Arg Lys Arg Ala Val Lys Leu Lys Asp Glu Ile His
            420                 425                 430

Arg Ser Met Asp Glu Gly Gly Val Ser Arg Met Glu Met Ala Ser Phe
        435                 440                 445

Ile Ala His Ile Ser Arg
    450

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: PCR Primer

<400> SEQUENCE: 13
catggagatg ggttctttca ttgcac                                          26

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 14
caacaactga agcactcacc aacg                                            24

<210> SEQ ID NO 15
<211> LENGTH: 28
<212> TYPE: DNA
<213> ORGANISM: Artificial Sequence
<220> FEATURE:

-continued

```
<223> OTHER INFORMATION: Description of Artificial Sequence: PCR Primer

<400> SEQUENCE: 15
ccaaagtcga caatggcttt gaatgatg                                              28

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: PCR Primer

<400> SEQUENCE: 16
gctatgcggc cgcctaaatg gtatgac                                               27
```

ENZYMES RESPONSIBLE FOR THE METABOLISM OF ZEATIN

CROSS-REFERENCE TO RELATED APPLICATIONS

This is a continuation of International Application No. PCT/US98/27759, filed Dec. 24, 1998, and claims the benefit of U.S. Provisional Application No. 60/080,852, filed Apr. 6, 1998, which applications are herein incorporated by reference.

GOVERNMENTAL SUPPORT

This invention was made with government support under grant number IBN-9116490, awarded by the National Science Foundation. The government has certain rights in the invention.

FIELD OF THE INVENTION

This invention relates to plant hormones, and in particular to cytokinins. Aspects of the invention include a purified zeatin O-glucosyltransferase enzyme, a purified zeatin O-xylosyltransferase enzyme, nucleic acid molecules encoding these enzymes, and vectors containing all or a portion of the nucleic acid molecules. Transgenic cells and transgenic plants having modified zeatin O-glucosyltransferase and/or modified zeatin O-xylosyltransferase activity are also provided. The invention also relates to altered plant traits in general, and seed development and yield in particular, resulting from the modification of zeatin O-glucosyltransferase and/or zeatin O-xylosyltransferase activity in plants.

BACKGROUND OF THE INVENTION

Cytokinins are plant hormones that mediate cell division and development. This group of hormones was discovered by Miller et al. (1955, 1956) with the identification of the first synthetic cytokinin, kinetin. The first naturally occurring cytokinin, zeatin, was discovered by Letham (1963) in corn and the structure of zeatin was determined by Shaw and Wilson (1964). Zeatin is the most active and ubiquitous cytokinin in all plant species examined. Other naturally occurring cytokinins are structurally related to zeatin (Shaw, 1994).

The critical importance of cytokinins in plant development was illustrated by the classic tissue culture experiments of Skoog et al. (1965). These experiments established that plant cell division requires cytokinin. Furthermore, the ratio of cytokinins to auxins (another group of plant hormones) was shown to determine whether undifferentiated plant cells will develop into shoots (high cytokinin to auxin), or roots (low cytokinin to auxin) or continue to proliferate as callus tissues (intermediate cytokinin to auxin ratio). Thereafter, cytokinin was found to be involved in every phase of plant growth (Mok 1994). In general, cytokinins have growth promoting effects, from seed germination and shoot development to retarding senescence and increasing fruit and seed set.

The effects of cytokinins in controlling plant growth have been extensively utilized in plant tissue culture to micropropagate and clone plants and to regenerate whole plants from cells of many species (Krikorian 1995). In fact, the application of cytokinins in vitro contributes significantly to advances in plant biotechnology. In agricultural applications, external applications of cytokinins on whole plants are used to obtain enhanced fruit set and grain yield of food crops and longer shelf life of ornamentals (Hradecka and Petr 1992; Karanov et al. 1992; Lewis et al. 1996; Minana et al. 1989).

Cytokinins are converted to various metabolites in plant tissues (Jameson 1994). For example, the metabolites of zeatin include O-xylosylzeatin, O-glucosylzeatin, N-glucosylzeatin, zeatin riboside and zeatin nucleotides. The precise functions of these metabolites are still uncertain. However, some of these metabolites may be the stored or the transported form of the active compound, zeatin. The O-glucoside of zeatin may be such a metabolite (Badenoch-Jones 1996). It was first discovered by Letham et al. (1976) and has been found in all crops examined including corn, beans, poplar and soybean. As O-glucosylzeatin can be readily converted back to its active form, zeatin, by the removal of the glucose moiety (via the action of the widespread β-glucosidase enzymes), it is considered a reversible reserve of active cytokinin (Brzobohaty et al. 1993). Also, O-glucosylzeatin is resistant to attack by cytokinin oxidases (McGaw and Horgan 1983) which degrade the parent compound, zeatin. Therefore, O-glucosylzeatin may be important in cytokinin action by serving as a remobilizable reserve and as a resistant form of zeatin.

The enzyme catalyzing the formation of zeatin to O-glucosylzeatin is termed zeatin O-glucosyltransferase. It was first purified and characterized in the inventor's laboratory (Dixon et al. 1989) from lima beans (*Phaseolus lunatus*) as part of a continuing effort to study the metabolism of zeatin (Mok and Martin 1994). The isolation of the enzyme was followed by the generation of specific antibodies that recognize the enzyme (Martin et al. 1990). Enzyme assays and immunoblotting (western) analysis indicated that zeatin O-glucosyltransferase occurs in small developing seeds. As seed size is determined by cell number and cell size, both factors influenced by the level of cytokinins, the occurrence of zeatin O-glucosyltransferase in immature seeds suggests that the enzyme is likely to be of critical importance in determining the eventual seed yield.

Another enzyme that converts zeatin into a metabolite was identified in 1987. This enzyme was termed zeatin O-xylosyltransferase (Turner et al. 1987). The enzyme mediates the formation of O-xylosylzeatin from zeatin using UDPX as the sugar donor. The enzyme has similar properties as zeatin O-glucosyltransferase isolated from *Phaseolus lunatus* but can be distinguished by substrate specificity and charge (Dixon et al. 1989). Briefly, the O-xylosyltransferase utilizes UDPX as the sugar donor while the O-glucosyltransferase uses both UDPG and UDPX but with much greater affinity to UDPG. The O-xylosyltransferase also has higher negative charge than O-xylosyltransferase as determined by anion exchange column chromatography.

Plants having modified endogenous zeatin activity would be of significant agricultural importance. Such plants could be created through genetic engineering if the genes regulating zeatin were available. It is to such genes that the present invention is directed.

SUMMARY OF THE INVENTION

The present invention provides isolated plant nucleic acid molecules (cDNA and genomic sequences) encoding zeatin O-glucosyltransferase, a key enzyme in the regulation of zeatin activity in plants. The present invention also provides isolated plant nucleic acid molecules encoding O-xylosyltransferase, another key enzyme in the regulation of zeatin activity in plants.

In one embodiment, the zeatin O-glucosyltransferase nucleic acids disclosed are from the lima bean, *Phaseolus*

*lunatus*. The open reading frame of these nucleic acid molecules encodes a polypeptide of 459 amino acids in length. This polypeptide is shown to have zeatin O-glucosyltransferase enzymatic activity i.e., it catalyzes the conversion of zeatin to O-glucosylzeatin. Accordingly, one aspect of the invention comprises isolated nucleic acid molecules encoding zeatin O-glucosyltransferase. Another aspect of the invention is the purified zeatin O-glucosyltransferase enzyme.

In another embodiment, the zeatin O-xylosyltransferase nucleic acids disclosed are from *Phaseolus vulgaris*. The open reading frame of these nucleic acid molecules encodes a polypeptide of 454 amino acids in length. This polypeptide is shown to have zeatin O-xylosyltransferase enzymatic activity i.e., it catalyzes the conversion of zeatin to O-xylosylzeatin. Accordingly, one aspect of the invention comprises isolated nucleic acid molecules encoding zeatin O-xylosyltransferase. Another aspect of the invention is the purified zeatin O-xylosyltransferase enzyme.

Also encompassed within the scope of this invention are transformation vectors which include at least a portion of the disclosed nucleic acid sequences. Such vectors may be transformed into plants to produce transgenic plants with modified zeatin O-glucosyltransferase activity and/or modified O-xylosyltransferase activity. Depending on the particular sequence incorporated into the vector, transformation with the zeatin O-glucosyltransferase cDNA and/or the O-xylosyltransferase cDNA, genes or derivatives thereof may be used to modify agronomically important traits, including the activity of zeatin in seeds, grain yield and seed germination rates. While all crop plants may benefit from such modified activity, it is anticipated that the invention will be particularly valuable in maize, wheat and legumes.

Typically, vectors used to modify zeatin O-glucosyltransferase activity and/or O-xylosyltransferase activity include regulatory sequences that are operably linked to the zeatin O-glucosyltransferase cDNA and/or zeatin O-xylosyltransferase cDNA, gene(s), or derivatives thereof. For example, zeatin O-glucosyltransferase activity may be modified in plants by introducing a transformation vector that includes a sense or antisense form of the disclosed cDNA operably linked to a high level constitutive promoter such as the 35S promoter of cauliflower mosaic virus. Transgenic plants transformed with such recombinant vectors and having modified zeatin O-glucosyltransferase activity and/or modified O-xylosyltransferase activity are part of the invention.

While the invention provides zeatin O-glucosyltransferase-encoding nucleic acids from *Phaseolous lunatus*, as well as zeatin O-xylosyltransferase-encoding nucleic acids from *Phaseolous vulgaris*, it additionally encompasses homologs, orthologs and derivatives of these sequences, as well as homologs, orthologs and variants of the zeatin O-glucosyltransferase polypeptide sequence and the zeatin O-xylosyltransferase polypeptide sequence. Thus, in one aspect of the invention, nucleic acid molecules that comprise specified regions of these sequences are provided. Exemplary of such nucleic acid molecules are oligonucleotides that are useful as probes or primers to detect and amplify zeatin O-glucosyltransferase-encoding nucleic acids and zeatin O-xylosyltransferase-encoding nucleic acids from other plant species. Such oligonucleotides are useful as hybridization probes or PCR primers, and typically comprise at least 15 consecutive bases of the disclosed sequences. In other embodiments, such oligonucleotides comprise longer regions of the disclosed sequences, such as at least 20, 25 or 30 consecutive nucleotides.

In another aspect, the invention provides compositions and methods for isolating nucleic acid sequences that have zeatin O-glucosyltransferase activity or zeatin O-xylosyltransferase activity from other plant species. Typically, such methods involve hybridizing probes or primers derived from the disclosed *P. lunatus* and *P. vulgaris* sequences to nucleic acids obtained or derived from such other plant species.

Homologous and orthologous sequences to the *P. lunatus* zeatin O-glucosyltransferase, or the *P. vulgaris* zeatin O-xylosyltransferase nucleic acid and amino acid sequences share key functional and structural characteristics with the disclosed Phaseolous sequences. Functionally, such sequences encode (or comprise) a polypeptide that either catalyzes the O-glucosylation of zeatin or the O-xylosylation of zeatin. Structurally, such sequences share a specified structural relationship with the disclosed sequences. By way of example, in certain embodiments, homologous amino acid sequences have at least 70% sequence identity with the *P. lunatus* zeatin O-glucosyltransferase amino acid sequence or the *P. vulgaris* zeatin O-xylosyltransferase amino acid sequence. In other embodiments, homologous nucleic acid sequences hybridize under stringent conditions to the disclosed *P. lunatus* zeatin O-glucosyltransferase nucleic acid sequences or the *P. vulgaris* O-xylosyltransferase nucleic acid sequences.

Another aspect of the invention relates to the purified zeatin O-glucosyltransferase enzyme, and the purified zeatin O-xylosyltransferase enzyme. Having provided nucleic acid molecules that encode these enzymes, the invention facilitates the expression of zeatin O-glucosyltransferase and/or zeatin O-xylosyltransferase in heterologous systems, including *E. coli*, yeast and baculovirus expression systems. Thus, the invention permits the large scale production of the enzymes for agricultural and other applications.

In another aspect of the invention the promoter sequence of the *P. lunatus* zeatin O-glucosyltransferase gene is disclosed. This promoter sequence confers seed-specific expression, and may be used to express a variety of nucleic acids in a seed-specific manner.

BRIEF DESCRIPTION OF THE DRAWINGS

FIG. 2A: cytokinin standards. FIG. 2B: reaction products after incubating $^{14}$C-zeatin with recombinant fusion protein. FIG. 2C: reaction products treated with O-glucosidase.

Figure 2:
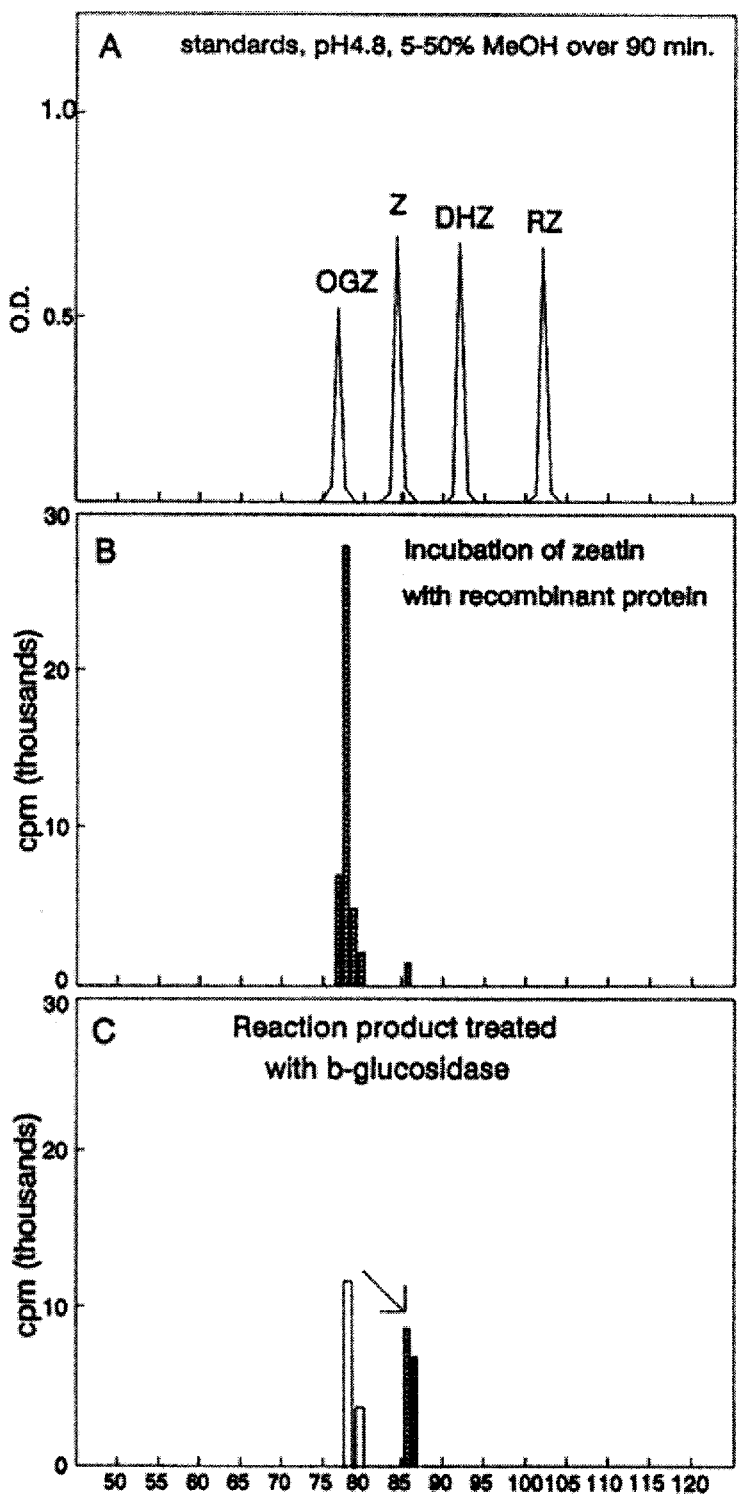
FIG. 2 is a graph showing the analysis of enzymatic reaction products by HPLC.

For FIG. 2B: 200 µl of supernatant obtained from cell culture was incubated with approximately 1 nmol of labeled zeatin and UDPG for 2 hrs. For FIG. 2C: Approximately 0.4 nmole of reaction product obtained from reactions similar to FIG. 2B was incubated with β-glucosidase for 4 hrs to reconvert the product to zeatin.

Figure 3:
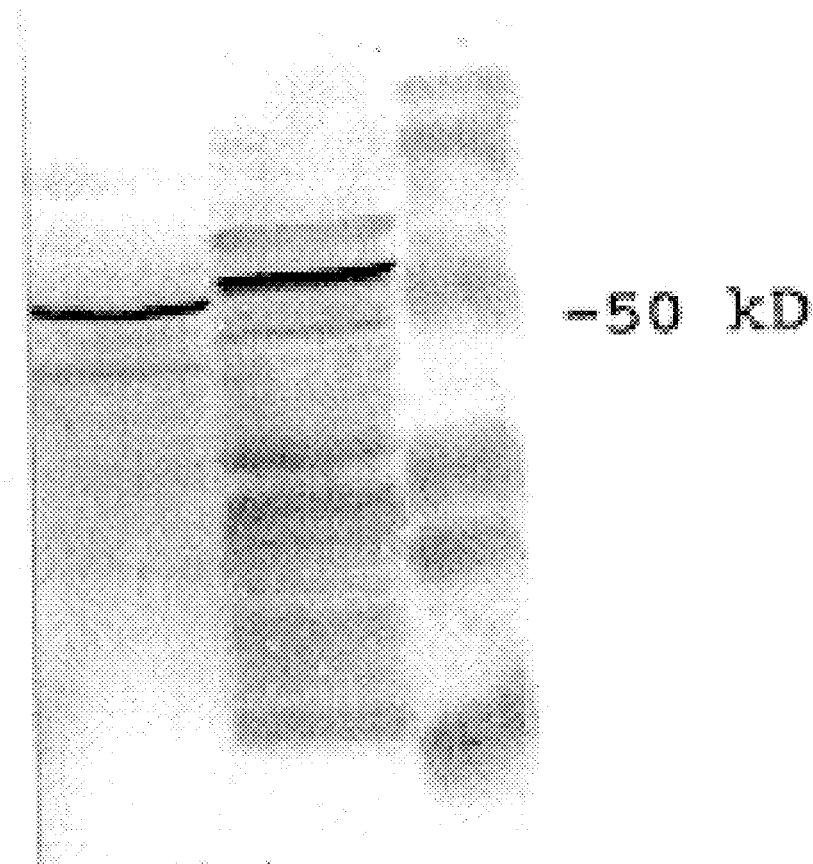

FIG. 3 shows the formation of O-xylosylzeatin from zeatin catalyzed by the enzyme zeatin O-xylosyltransferase.

SEQUENCE LISTING

The nucleic and amino acid sequences listed in the accompanying sequence listing are shown using standard letter abbreviations for nucleotide bases, and three letter code for amino acids. Only one strand of each nucleic acid sequence is shown, but the complementary strand is understood to be included by any reference to the displayed strand.

Seq. I.D. No. 1 shows the nucleic acid sequence of the *Phaseolous lunatus* zeatin O-glucosyltransferase cDNA. The sequence includes the 5' untranslated region (base pairs 1–32) and the open reading frame (base pairs 33–1412).

Seq. I.D. No. 2. shows the nucleic acid sequence of the *Phaseolous lunatus* zeatin O-glucosyltransferase gene. The sequence includes the TATA-like region (base pairs 29–34) and the open reading frame (base pairs 142–1521).

Seq. I.D. No. 3 shows the nucleic acid sequence of the *Phaseolous lunatus* zeatin O-glucosyltransferase open reading frame.

Seq. I.D. No. 4 shows the amino acid sequence of the *Phaseolous lunatus* zeatin O-glucosyltransferase polypeptide.

Seq. I.D. No. 5 shows the amino acid sequence of the 56 kDa. fusion protein. This fusion protein comprises 33 amino acids of the α-peptide encoded by the vector (amino acids 1–33) and the 5' untranslated region (amino acids 34–44) and the open reading frame (amino acids 45–503) of zeatin O-glucosyltransferase.

Seq. I.D. No. 6 shows the seed-specific promoter region of the *Phaseolous lunatus* zeatin O-glucosyltransferase gene.

Seq. I.D. Nos. 7–10 show primers that may be used to amplify various regions of the zeatin O-glucosyltransferase cDNA sequence.

Seq. I.D. No. 11 shows the nucleic acid sequence of the *Phaseolous vulgaris* zeatin O-xylosyltransferase open reading frame.

Seq. I.D. No. 12 shows the deduced amino acid sequence of the open reading frame of the *Phaseolous vulgaris* zeatin O-xylosyltransferase.

Seq. I.D. Nos. 13 and 14 show primers that may be used in conjunction with inverse PCR to identify sequences related to the zeatin O-glucosyltransferase sequence.

Seq. I.D. Nos. 15 and 16 show primers that may be used to amplify various regions of the zeatin O-xylosyltransferase cDNA sequence.

DETAILED DESCRIPTION OF THE INVENTION

I. Definitions and Abbreviations

A. Abbreviations
[$^{14}$C]zeatin: trans-[8-$^{14}$C]zeatin
Cis-Z: Cis-zeatin
Z: trans-zeatin
OGZ: O-glucosylzeatin
OXZ: O-xylosylzeatin
DHZ: dihydrozeatin
OXDHZ: O-xylosyldihydrozeatin
RZ: ribosylzeatin
OXRZ: O-xylosylribosylzeatin
UDPG: uridine diphosphate glucose
UDPX: uridine diphosphate xylose
ADPG: adenosine diphosphate glucose
TEA: triethylamine
ORF: open reading frame
MAb: monoclonal antibody B. Definitions Unless otherwise noted, technical terms are used according to conventional usage. Definitions of common terms in molecular biology may be found in Benjamin Lewin, *Genes V* published by Oxford University Press, 1994 (ISBN 0-19-854287-9); Kendrew et al (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). The nomenclature for DNA bases as set forth at 37 CFR §1.822 and the standard three letter codes for amino acid residues are used herein.

Figure 1:
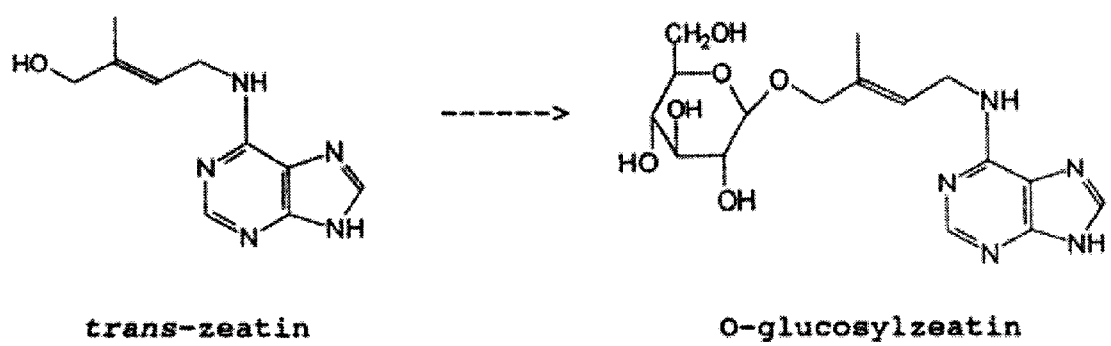
FIG. 1 shows the formation of O-glucosylzeatin from zeatin catalyzed by the enzyme zeatin O-glucosyltransferase.

In order to facilitate review of the various embodiments of the invention, the following definitions of terms is provided:

Zeatin O-glucosyltransferase: The defining functional characteristic of the zeatin O-glucosyltransferase enzyme is its ability to glucosylate cytokinins, such as zeatin. By way of example, the Phaseolous zeatin O-glucosyltransferase is capable of glucosylating zeatin to form O-glucosylzeatin, a conversion that is depicted in FIG. 1. This activity can be measured using the assay described by Dixon et al. (1989), which is described in detail below. This invention provides a cDNA and a gene encoding the zeatin O-glucosyltransferase enzyme from *Phaseolous lunatus*. However the invention is not limited to this particular zeatin O-glucosyltransferase: other nucleotide sequences which encode zeatin O-glucosyltransferase enzymes are also part of the invention, including variants on the disclosed Phaseolous cDNA and gene sequences and orthologous sequences from other plant species, the cloning of which is now enabled. Such sequences share the essential functional characteristic of encoding an enzyme that is capable of glucosylating cytokinins. Nucleic acid sequences that encode zeatin O-glucosyltransferases and the proteins encoded by such nucleic acids share not only this functional characteristic, but also a specified level of sequence similarity (or sequence identity), as addressed below. The concept of sequence identity can also be expressed in the ability of two sequences to hybridize to each other under stringent conditions.

Zeatin O-xylosyltransferase: The defining functional characteristic of the zeatin O-xylosyltransferase enzyme is its ability to xylosylate cytokinins, such as zeatin. By way of example, the Phaseolous zeatin O-xylosyltransferase is capable of xylosylating zeatin to form O-xylosylzeatin, a conversion that is depicted in FIG. 3. This activity can be measured using the assay described by Dixon et al. (1989), which is described in detail below. This invention provides a cDNA encoding the zeatin O-xylosyltransferase enzyme from *Phaseolous vulgaris*. However the invention is not limited to this particular zeatin O-xylosyltransferase: other nucleotide sequences which encode zeatin O-xylosyltransferase enzymes are also part of the invention, including variants on the disclosed Phaseolous cDNA and gene sequences and orthologous sequences from other plant species, the cloning of which is now enabled. Such sequences share the essential functional characteristic of encoding an enzyme that is capable of xylosylating cytokinins. Nucleic acid sequences that encode zeatin O-xylosyltransferases and the proteins encoded by such nucleic acids share not only this functional characteristic, but also a specified level of sequence similarity (or sequence identity), as addressed below. The concept of sequence identity can also be expressed in the ability of two sequences to hybridize to each other under stringent conditions.

Sequence identity: the similarity between two nucleic acid sequences, or two amino acid sequences is expressed in terms of sequence identity. Sequence identity is frequently measured in terms of percentage identity (or similarity or homology); the higher the percentage, the more similar the two sequences are.

The calculation of percentage of sequence identity for amino acid sequences may take into account conservative amino acid substitutions. Conservative amino acid substitutions involve the replacement of one amino acid residue with another residue having similar chemical and biological properties (e.g., charge or hydrophobicity). Such substitutions typically do not change the functional properties of the protein, and should therefore be accounted for in the calculation of sequence identity by assigning a value that is in between values assigned for identity (i.e., no change at that amino acid position) and non-conservative residue changes. Thus, conservative amino acid changes are scored as a partial rather than a full mismatch, thereby increasing the percentage sequence identity. For example, if an identical amino acid is given a score of one and a non-conservative substitution is given a score of zero, a conservative substitution might be given a score of 0.5. The scoring of conservative substitutions is calculated, e.g., according to the algorithm of Meyers and Miller (1988) e.g., as implemented in the program PC/GENE (Intelligenetics, Mountain View, Calif., USA).

Methods of alignment of sequences for comparison are well-known in the art. Various programs and alignment algorithms are described in: Smith and Waterman (1981); Needleman and Wunsch (1970); Pearson and Lipman (1988); Higgins and Sharp (1988); Higgins and Sharp (1989); Corpet et al. (1988); Huang et al. (1992); and Pearson et al. (1994). Altschul et al. (1994) presents a detailed consideration of sequence alignment methods and homology calculations.

The NCBI Basic Local Alignment Search Tool (BLAST) (Altschul et al., 1990) is available from several sources, including the National Center for Biological Information (NCBI, Bethesda, Md.) and on the Internet, for use in connection with the sequence analysis programs blastp, blastn, blastx, tblastn and tblastx. It can be accessed at http//www.ncbi.nlm.nih.gov/BLAST/. A description of how to determine sequence identity using this program is available at http://www.ncbi.nlm.nih.gov/BLAST/blast help.html.

Homologs of the Phaseolous zeatin O-glucosyltransferase and zeatin O-xylosyltransferase proteins are characterized by possession of at least 70% sequence identity counted over the full length alignment with the disclosed Phaseolous amino acid using the NCBI Blast 2.0, gapped blastp set to default parameters. Such homologous peptides will more preferably possess at least 75%, more preferably at least 80% and still more preferably at least 90% or 95% sequence identity determined by this method. When less than the entire sequence is being compared for sequence identity, homologs will possess at least 75% and more preferably at least 85% and more preferably still at least 90% or 95% sequence identity over short windows of 10–20 amino acids. Methods for determining sequence identity over such short windows are described at http://www.ncbi.nlm.nih.gov/BLAST/blast FAQs.html. Homologs having the sequence identities described above will, in some embodiments, also possess the ability to O-glucosylate zeatin or O-xylosylate zeatin. The present invention provides not only the peptide homologs described above, but also nucleic acid molecules that encode such homologs.

Homologs of the Phaseolous zeatin O-glucosyltransferase and zeatin O-xylosyltransferase cDNA as well as homologs of the zeatin O-glucosyltransferase gene are similarly characterized by possession of at least 60% sequence identity counted over the full length alignment with the disclosed Phaseolous cDNAs or gene sequences using the NCBI Blast 2.0, gapped blastn set to default parameters. Such homologous nucleic acids will more preferably possess at least 70%, more preferably at least 80% and still more preferably at least 90% or 95% sequence identity determined by this method. When less than the entire sequence is being compared for sequence identity, homologs will possess at least 85% and more preferably at least 90% and more preferably still at least 95% sequence identity over 30 nucleotide windows. Homologs having the sequence identities described above will, in some embodiments, also encode a polypeptide having ability to O-glucosylate or O-xylosylate zeatin. However, homologs as defined above are useful for modifying zeatin O-glucosyltransferase activity and/or zeatin O-xylosyltransferase activity in transgenic plants (for example, as used in antisense constructs) even when they do not encode a functional peptide.

Another indication that two nucleic acid molecules are substantially homologous is that the two molecules hybridize to each other under stringent conditions when one molecule is used as a hybridization probe, and the other is present in a biological sample, e.g., genomic material from a cell. Specific hybridization means that the molecules hybridize substantially only to each other and not to other molecules that may be present in the genomic material. Stringent conditions are sequence dependent and are different under different environmental parameters. Generally, stringent conditions are selected to be about 5° C. to 20° C. lower than the thermal melting point (Tm) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. (1989) and Tijssen (1993). Hybridization conditions and stringencies are further discussed below.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequence that all encode substantially the same protein.

Probes and primers: Nucleic acid probes and primers may readily be prepared based on the nucleic acids provided by this invention. A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al. (1989) and Ausubel et al. (1987).

Primers are short nucleic acids, preferably DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (1989), Ausubel et al. (1987), and Innis et al., (1990). PCR primer pairs can be derived from a known sequence, for example, by using computer programs intended for that purpose such as Primer (Version 0.5, ©1991, Whitehead Institute for Biomedical Research, Cambridge, Mass.). One of skill in the art will appreciate that the specificity of a particular probe or primer increases with its length. Thus, for example, a primer comprising 20 consecutive nucleotides of the Phaseolous zeatin O-glucosyltransferase cDNA or gene will anneal to a target sequence (e.g., a corresponding zeatin O-glucosyltransferase from *Zea mays*) with a higher specificity than a corresponding primer of only 15 nucleotides. Thus, in order to obtain greater specificity, probes and primers may be selected that comprise 20, 25, 30, 35, 40, 50 or more consecutive nucleotides of the Phaseolous zeatin O-glucosyltransferase cDNA or gene sequences.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Isolated: An "isolated" biological component (such as a nucleic acid or protein) has been substantially separated or purified away from other biological components in the cell of the organism in which the component naturally occurs, i.e., other chromosomal and extrachromosomal DNA and RNA, and proteins. Nucleic acids and proteins which have been "isolated" thus include nucleic acids and proteins purified by standard purification methods. The term also embraces nucleic acids and proteins prepared by recombinant expression in a host cell as well as chemically synthesized nucleic acids.

Purified: The term purified does not require absolute purity; rather, it is intended as a relative term. Thus, for example, a purified zeatin O-glucosyltransferase preparation is one in which the zeatin O-glucosyltransferase is more enriched than the protein is in its natural environment within a cell. Preferably, a preparation of zeatin O-glucosyltransferase is purified such that the zeatin O-glucosyltransferase represents at least 50% of the total protein content of the preparation.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Ortholog: two nucleotide or amino acid sequences are orthologs of each other if they share a common ancestral sequence and diverged when a species carrying that ancestral sequence split into two species. Orthologous sequences are also homologous sequences.

Transgenic plant: as used herein, this term refers to a plant that contains recombinant genetic material not normally found in plants of this type and which has been introduced into the plant in question (or into progenitors of the plant) by human manipulation. Thus, a plant that is grown from a plant cell into which recombinant DNA is introduced by transformation is a transgenic plant, as are all offspring of that plant which contain the introduced DNA (whether produced sexually or asexually).

II. Isolation of cDNA and Genomic Sequences encoding Zeatin O-glucosyltransferase and Zeatin O-xylosyltransferase from Phaseolous.

A. Overview of Experimental Procedures

The experimental procedure used to isolate the zeatin O-glucosyltransferase nucleic acid sequence involved creating a cDNA expression library and probing the library using a monoclonal antibody to zeatin O-glucosyltransferase. The clones that reacted with the antibody were transformed into a bacterial expression system that allowed a larger amount of the protein to be isolated. The isolated protein was then tested for zeatin O-glucosyltransferase activity.

Clones that contained the appropriate enzymatic activity were subjected to partial sequencing. This process allowed primers to be made that were specific to the newly isolated sequence. Subsequent use of inverse PCR allowed the entire gene to be isolated from genomic DNA. The PCR product from the genomic DNA was then cloned into a pGem-T vector (Promega) for complete sequencing.

The O-xylosyltransferase cDNA was identified through the use of inverse PCR followed by PCR. The inverse PCR primers were designed using the knowledge of the zeatin O-glucosyltransferase gene sequence. The sequence derived from the inverse PCR reaction then allowed specific PCR primers to be made. Finally, the PCR product was cloned into a pGem-T vector for complete sequencing.

Expression of the zeatin O-xylosyltransferase gene was achieved by subcloning the sequence into an inducible expression vector. The expressed protein was then isolated and tested for enzymatic activity.

B. Methods

Construction of cDNA expression library and screening with MAbs to zeatin O-glucosyltransferase. Total RNA was isolated from immature seeds of *P. lunatus* using TRI REAGENT (Molecular Research Center, Inc., Cincinnati, Ohio) following the manufacturer's protocols with modifications for samples with a high content of polysaccharides. mRNA was further enriched with the Promega PolyATract mRNA isolation system according to manufacturer's instructions (Promega, Madison, Wis.). An expression library was constructed using the SuperScript™ Lambda System for cDNA sysnthesis and lambda ZipLox cloning (BRL Life Technologies, Inc.). First strand synthesis was primed with a NotI-oligo-d(T) primer-adapter. Following second strand synthesis SalI adapters were ligated to the cDNA, which was subsequently digested with NotI. This allowed for directional cloning of cDNA into the lambda ZipLox expression vector (Gibco BRL, Gaithersburg, Md.). The constructed lambda cDNA library was packaged following the manufacturer's instructions (BRL lambda packaging system). The lambda ZipLox cDNA library was plated with *E. coli* Y1090(ZL) on top agar and incubated at 37° C. for 3–4 hours. The plates were then overlaid with nitrocellulose filters which had been presoaked with 10 mM IPTG and dried, and incubated at 37° C. overnight. Filters were marked for orientation, removed from the plates, and washed briefly in TBS. The membranes were blocked in TBS containing 2% nonfat dry milk for 1–2 hours at room temperature with constant agitation. Filters were then incubated with blocking solution containing primary antibody for 2 hours at 30° C. Filters were washed three times (5 minutes each) in blocking solution. Secondary antibody (Rabbit anti-mouse conjugated to Alkaline Phosphatase, Jackson Laboratories) in blocking solution was applied to the filters for 2 hours at 30° C. Filters were washed and the positive clones identified with an Alkaline Phosphatase Substrate Kit (Vector Laboratories, Burlingame, Calif.). Immunopositive plaques were removed, replated, and rescreened until pure plaques were obtained.

Subcloning and sequencing of the zeatin O-glucosyltransferase cDNA. The phage containing the lambda ZipLox vector harboring the insert was used to infect E. coli cell line DH10B(ZIP), thus allowing in vivo excision of the cDNA clone from the pZL1 plasmid. pZL1 clones were purified using Qiagen Midi Columns (Qiagen, Chatsworth, Calif.). Clones were sequenced using an Applied Biosystems 370A DNA sequence analyzer. Primers synthesized on an Applied Biosystems DNA Synthesizer were used for sequencing the inner portions of the clones.

Isolation of recombinant zeatin O-glucosyltransferase proteins. To obtain recombinant proteins, purified plasmids were transformed into Epicurian Coli BL21(DE3) pLysS Competent cells (Stratagene, LaJolla, Calif.) following the recommended protocol. Colonies were selected on AMP-LB plates. An individual colony was grown overnight in SOC-AMP media and 0.5 ml of the culture was used to inoculate 50 mls of SOC-AMP media. Induction was achieved with IPTG (0.5 ml of 0.5 M) after cells were allowed to grow for 3–4 hours (OD at 595 nm of 0.8–1.0). After 4 hours cells were collected and frozen at −80° C. overnight. Cells were lysed the next day by thawing and resuspending in 0.5 ml of 0.2 M Tris pH 7.5 containing 1 mg/ml of lysozyme. DNAase (1 $\mu$g/10 $\mu$l sample) was added after a 10-min. cycle of freeze-thaw at −80° C. Soluble proteins were collected after centrifugation. Recombinant proteins were further purified on a DEAE anion exchange column using the Bio-Rad Biologic liquid chromatography system.

Isolation of genomic sequence of zeatin O-glucosyltransferase from P. lunatus. Isolation of the genomic sequence was based on the principles of PCR, and both standard and inverse PCR (Ochman et al. 1989) were used. DNA was isolated from P. lunatus cv. Kingston using a modified CTAB (hexadecyltrimethylammonium bromide) method (Doyle and Doyle 1990). PCR and inverse PCR was performed with primers homologous to the 5' and 3' regions of the cDNA clone. To obtain the genomic sequence upstream and downstream of the cDNA using inverse PCR, the genomic DNA was digested with HindIII. After digestion, the restriction enzyme was inactivated by heating the sample to 75° C. for 10 minutes. After dilution, $T_4$ DNA ligase (Promega) was added to allow intramolecular ligation (circularization). The reaction was performed at 15° C. for 24 hours. The DNA was precipitated and PCR reaction performed with primers designed to amplify regions outside the cDNA.

To obtain genomic sequence inclusive of the expressed region (cDNA), standard PCR reactions were performed using pairs of primers based on the sequence of the cDNA. The products obtained from PCR and inverse PCR reactions were analyzed on a 1% Sea Plaque gel. Bands of interest were excised and DNA was purified with Qiaex II Gel Extraction Kit (Qiagen, Santa Clarita, Calif.). The products were ligated into a pGem-T vector (Promega) for sequencing.

Isolation of zeatin O-xylosyltransferase genomic sequence. The sequence derived from the cloning of the zeatin O-glucosyltransferase gene allowed primers to be designed such that homologous genes could be identified. One such homologous gene was zeatin O-xylosyltransferase. This gene was identified through the use of inverse PCR, as described above. Briefly, DNA from P. vulgaris was digested with HindIII restriction enzyme, re-ligated and used as template for inverse PCR with the following primers, taken from the P. lunatus zeatin O-glucosyltransferase cDNA sequence:

5'-CAT GGA GAT GGG TTC TTT CAT TGC AC-3' (Seq. I.D. No. 13)

5'-CAA CAA CTG AAG CAC TCA CCA ACG-3' (Seq. I.D. No. 14)

The sequence derived from the inverse PCR product was then compared to the zeatin O-glucosyltransferase sequence and upon finding regions of non-homology, specific primers were made to the inverse PCR product sequence. These primers were as follows:

5'-CCA AAG TCG ACA ATG GCT TTG AAT GAT G-3' (Seq. I.D. No. 15)

5'-GCT ATG CGG CCG CCT AAA TGG TAT GAC-3' (Seq. I.D. No. 16)

The O-xylosyltransferase gene was then amplified using these primers in a PCR reaction with P. vulgaris genomic DNA as a template. The products were then ligated into a pGem-T vector (Promega) for sequencing.

Isolation of recombinant zeatin O-xylosyltransferase proteins. Zeatin O-xylosyltransferase protein was purified using the same techniques as described above. Briefly, the coding sequences were ligated into an IPTG inducible plasmid which was transformed into Epicurian Coli BL21(DE3) pLysS Competent cells (Stratagene, LaJolla, Calif.). IPTG was then used to induce protein. Cells were subsequently lysed and the protein was separated out through the use of ion exchange chromatography.

Assay for cytokinin conversion activity and analysis of reaction products. Enzyme activity (zeatin O-glucosyltransferase and zeatin O-xylosyltransferase) was determined using the method of Dixon et al. (1989), which is incorporated herein by reference. Briefly, $^{14}$C-labeled cytokinins (specific activity of 24 mCi/mmol), glycosyl donor (3 mM of UDPG or UDPX), $MgCl_2$ (0.05M) and ATP (0.5 mM) in 1 mM Tris, pH 8.0 were incubated with a specified amount of the recombinant protein at 27° C. One mL of cold ethanol was added after one hour, and the mixture was placed at 4° C. for 15 minutes and then centrifuged at 27,000 g for 20 minutes. The supernatant was concentrated to 100 $\mu$l in vacuo (Speed Vac Concentrator, Savant) and analyzed by HPLC using a reversed phase $C_{18}$column.

For HPLC analysis (also performed as described by Dixon et al., 1989), a Beckman model 110A dual pump HPLC system with a reversed-phase column (Ultrasphere ODS $C_{18}$, 5 $\mu$M particle size, 4.6×250 mm; Altex) was used. The aqueous buffer consisted of 0.2M acetic acid adjusted to pH 3.5 with TEA. Samples were eluted with a linear gradient of methanol (5–50% over 90 minutes) in TEA buffer. The flow rate was 1 mL/min. and 0.5 mL fractions were collected. A combination of a Beckman model 117 flow-through isotope detector and Isco UV monitor allowed the initial detection of fractions of interest. Radioactivity in these fractions was determined in Ready-Gel scintillation fluid (Beckman) with a Beckman LS 7000 scintillation counter.

C. Results

Isolation and authentication of zeatin O-glucosyltransferase cDNA clones. Approximately $10^6$ plaques were screened with the MAb and nine immunopositive lambda clones were selected. These were plaque purified and moved into cell line DH10B(ZIP) to allow circularization of the Zip-Lox plasmid containing the respective inserts. Epicurian Coli BL21 (DE3) pLysS cells (Strategene, LaJolla, Calif.) transformed with the purified plasmids were used to obtain the recombinant fusion proteins after IPTG induction. Supernatants were assayed for zeatin O-glucosyltransferase activity and for the presence of antigenic proteins by Western analysis. Recombinant protein from two clones, 21G and 27G, efficiently converted $^{14}$C-zeatin to $^{14}$C-O-glucosylzeatin (FIG. 2B) with UDPG as the glucosyl donor. The authenticity of the O-glucosyl product was confirmed by treatment with β-glucosidase resulting in reconversion to zeatin (FIG. 2C). Western analyses confirmed the presence of antigenic protein of the expected size (56 kD) for the fusion protein (the polypeptide encoded by the ORF plus the 5' untranslated region and the α-peptide from the cloning vector). The native zeatin O-glucosyltransferase of *P. lunatus* also uses UDPX as the donor to form O-xylosylzeatin but at a much lower affinity (Dixon et al. 1989).

To further test the authenticity of the recombinant protein encoded by clone 21G, UDPX was used as the glycosyl donor under the same reaction condition. As expected, O-xylosylzeatin was formed (see Table 1) but the amount was much lower. These results indicate that the selected cDNAs encode the correct sequence for zeatin O-glucosyltransferase. A trace of O-glucosyldihydrozeatin was formed when labeled dihydrozeatin was incubated with the DEAE-column purified recombinant protein.

TABLE 1

Substrate Specificity of Recombinant Zeatin O-glucosyltransferase Encoded by a Clone from the cDNA Library

| Substrates | Product CPM (%) | Substrate Left CPM (%) |
|---|---|---|
| A. Z + UDPG | OGZ | Zeatin |
| | 39715 (100%) | 0 (0%) |
| Z + UDPX | OXZ | Zeatin |
| | 4956 (18%) | 23078 (82%) |
| B. Z + UDPG | OGZ | Zeatin |
| | 3731 (14%) | 23115 (86%) |
| DHZ + UDPG | O-G-DH-Zeatin | DHZ |
| | 329 (1%) | 24178 (99%) |

A. 200 μl of supernatant from lysed cells containing the recombinant protein was incubated with approximately 1 nmole of $^{14}$C-labeled zeatin for 2 hr. and the reaction products separated by HPLC. UDPG as the glycosyl donor resulted in complete conversion of zeatin to O-glucosylzeatin while UDPX serving as the glycosyl donor resulted in much lower formation of O-xylosylzeatin.
B. DEAE-purified proteins (4 μg) were incubated with approximately 0.5 nmole of $^{14}$C-cytokinin Isolation and authentication of zeatin O-xylosyltransferase cDNA clones. To assess the enzyme activity of the protein encoded by zeatin O-xylosyltransferase, the ORF of the gene was excised from the pGem-T vector (Promega) using the restriction enzymes Not1 and Sal1. The resulting fragment was then ligated into the Not1/Sal1 site of the pZipLox plasmid. This ligation resulted in an in-frame construct producing a fusion protein (with α-peptide) of 54 kD which is also antigenic to the monoclonal antibody (Martin et al. 1990). This allowed for the recombinant protein to be easily purified.

The product has high enzyme activity, converting radio-labeled zeatin to O-xylosylzeatin in the presence of UDPX (Table 2). The substrate specificity and the properties of the recombinant protein are identical to those of the native enzyme (Table 2). The result indicated that the clone encoded the zeatin O-xylosyltranferase protein.

TABLE 2

Substrate Specificity of Recombinant Protein Encoded by the ORF of Zeatin O-xylosyltranferase

| Substrates | Product CPM (%) | Substrate Left CPM (%) |
|---|---|---|
| Z + UDPX | OXZ | Z |
| | 35838 (82%) | 7768 (18%) |
| Z + UDPG | OGZ | Z |
| | ND. | 41679 (100%) |
| DHZ + UDPX | OXDHZ | DHZ |
| | 33237 (78%) | 9244 (22%) |
| cis-Z + UDPX | OX-cis-Z | cis-Z |
| | ND. | 29460 (100%) |
| RZ + UDPX | OXRZ | RZ |
| | ND. | 39238 (100%) |

Assay conditions: 125 μl of protein from culture supernatant was incubated with radio-labeled cytokinins and UDPX or UDPG as indicated for 4 hrs. Reaction products were separated by HPLC according to Dixon et al. 1989.

Distinguishing Zeatin O-glucosyltransferase from Zeatin O-xylosyltransferase. A comparison between the results provided in Table 1, and the results provided in Table 2, confirms that the newly isolated recombinant zeatin O-glucosyltransferase protein and newly isolated recombinant zeatin O-xylosyltransferase protein are functionally distinguishable. As shown in Table 2, the isolated zeatin O-xylosyltransferase protein was specific for the UPDX substrate. In fact there was no detectable conversion of zeatin when UDPG was used as the sugar donor (Table 2). However, when zeatin O-glucosyltransferase was used under the same reaction conditions 100% of the zeatin was utilized to form OGZ (Table 1).

Sequence of Zeatin O-glucosyltransferase cDNA. The sequence of zeatin O-glucosyltransferase cDNA obtained from *P. lunatus* is presented in Seq. I.D. No. 1. The ORF (open reading frame) is shown separately in Seq. I.D. No. 3. The cDNA is 1.5 kb long and contains NcoI and HindIII restriction sites. BLAST search of GENBANK and EMBL located no sequences showing significant homology. The amino acid sequence of the zeatin O-glucosyltransferase polypeptide is shown in Seq. I.D. No. 4.

Genomic sequence of zeatin O-glucosyltransferase of *P. lunatus*. The genomic sequence of zeatin O-glucosyltransferase is presented in Seq. I.D. No. 2. The sequence contains no introns. The TATA-like region is located around base-pairs 29–34.

Genomic sequence of zeatin O-xylosyltransferase of *P. vulgaris*. A genomic clone of 1390 bp was obtained from *Phaseolous vulgaris* cv. Great Northern. The sequence of the product was determined. The gene contains an ORF of 1365 bp (Seq. I.D. No. 11) encoding a polypeptide of 454 amino acids (Seq. I.D. No. 12) with the deduced mass of 51.0 kD.

Comparison of the zeatin O-glucosyltransferase and the zeatin O-xylosyltransferase genes. Like the zeatin O-glucosyltransferase gene, the zeatin O-xylosyltransferase gene does not contain introns. Additionally, the nucleotide sequences of the two genes are very similar with the percent identity at 93.0% over 1,380 base pairs of the zeatin O-glucosyltransferase ORF sequence (Seq. I.D. 3). The deduced amino acid sequences have a percent similarity of 90.4% and a percent identity of 86.6% over 449 amino acids. These comparisons were determined using the program BESTFIT, with a gap setting of 12 which is available from Genetic Computing Group, Madison, Wis.

EXAMPLES

The following examples are illustrative of various embodiments of the present invention.

Example One

Preferred Method for Producing Zeatin O-glucosyltransferase and Zeatin O-xylosyltransferase Nucleic Acids With the provision herein of the zeatin O-glucosyltransferase cDNA sequence, the zeatin O-glucosyltransferase gene sequence and the zeatin O-xylosyltransferase ORF sequence (the disclosed Phaseolous sequences), the polymerase chain reaction (PCR) may now be utilized in a preferred method for producing nucleic acid sequences encoding zeatin O-glucosyltransferase or zeatin O-xylosyltransferase. PCR amplification of the disclosed Phaseolous sequences may be accomplished either by direct PCR from a plant cDNA library or by Reverse-Transcription PCR (RT-PCR) using RNA extracted from plant cells as a template. Methods and conditions for both direct PCR and RT-PCR are known in the art and are described in Innis et al. (1990). Suitable plant cDNA libraries for direct PCR include the Arabidopsis cDNA library described by Newman et al. (1994) and Phaseolous cDNA libraries constructed as described above.

The selection of PCR primers will be made according to the portions of the cDNA or gene that are to be amplified. Primers may be chosen to amplify small segments of the cDNA, the open reading frame, the entire cDNA molecule or the entire gene sequence. Variations in amplification conditions may be required to accommodate primers of differing lengths; such considerations are well known in the art and are discussed in Innis et al. (1990), Sambrook et al. (1989), and Ausubel et al. (1992). By way of example only, the entire zeatin O-glucosyltransferase cDNA molecule as shown in Seq. I.D. No. 1 may be amplified using the following combination of primers:

5'-GAAGCATAGCATCTTGCTACC-3' (Seq. I.D. No. 7)
5'-CAACAGAAGCTTTATTATTGG-3' (Seq. I.D. No. 8)

The open reading frame portion of the cDNA may be amplified using the following primer pair:

5'-ATGGCTTTGAATGACAAAAGC-3' (Seq. I.D. No. 9)
5'-CTATTTAGAGATGTGTGCAATG-3' (Seq. I.D. No. 10)

These primers are illustrative only; it will be appreciated by one skilled in the art that many different primers may be derived from the provided cDNA and gene sequences in order to amplify particular regions of these molecules. Resequencing of PCR products obtained by these amplification procedures is recommended; this will facilitate confirmation of the amplified sequence and will also provide information on natural variation on this sequence in different ecotypes and plant populations.

Oligonucleotides that are derived from the disclosed Phaseolous sequences are encompassed within the scope of the present invention. Preferably, such oligonucleotide primers will comprise a sequence of at least 15–20 consecutive nucleotides of the disclosed Phaseolous sequences. To enhance amplification specificity, oligonucleotide primers comprising at least 25, 30, 35, 40, 45 or 50 consecutive nucleotides of these sequences may also be used.

Example Two

Isolation of Homologous Gene Sequence From other Plant Species

With the provision herein of the disclosed Phaseolous sequences, the cloning of orthologous cDNAs and genes from other plant species by standard methodologies is now enabled. Thus, the present invention includes methods of isolating both cDNA and genomic sequences encoding zeatin O-glucosyltransferase and zeatin O-xylosyltransferase. Both conventional hybridization and PCR amplification procedures may be utilized to clone such sequences. Common to both of these techniques is the hybridization of probes or primers derived from the disclosed Phaseolous sequences to a target nucleotide preparation, which may be, in the case of conventional hybridization approaches, a cDNA or genomic library or, in the case of PCR amplification, a cDNA or genomic library, or an mRNA preparation.

Direct PCR amplification may be performed on cDNA or genomic libraries prepared from the plant species in question, or RT-PCR may be performed using mRNA extracted from the plant cells using standard methods. PCR primers will comprise at least 15 consecutive nucleotides of the disclosed Phaseolous sequences. One of skill in the art will appreciate that sequence differences between the disclosed Phaseolous sequences and the target nucleic acid to be amplified may result in lower amplification efficiencies. To compensate for this, longer PCR primers or lower annealing temperatures may be used during the amplification cycle. Where lower annealing temperatures are used, sequential rounds of amplification using nested primer pairs may be necessary to enhance specificity.

For conventional hybridization techniques (described further in Example four below) the hybridization probe is preferably conjugated with a detectable label such as a radioactive label, and the probe is preferably of at least 20 nucleotides in length. As is well known in the art, increasing the length of hybridization probes tends to give enhanced specificity. The labeled probe derived from the Phaseolous cDNA or gene sequence may be hybridized to a plant cDNA or genomic library and the hybridization signal detected using means known in the art. The hybridizing colony or plaque (depending on the type of library used) is then purified and the cloned sequence contained in that colony or plaque isolated and characterized.

Homologs of the Phaseolous zeatin O-glucosyltransferase and Phaseolous zeatin O-xylosyltransferase may alternatively be obtained by immunoscreening of an expression library. With the provision herein of the disclosed Phaseolous nucleic acid sequences, the enzymes may be expressed and purified in a heterologous expression system (e.g., E. coli) and used to raise antibodies (monoclonal or polyclonal) specific for the zeatin O-glucosyltransferase protein or the zeatin O-xylosyltransferase protein. Antibodies may also be raised against synthetic peptides derived from the Phaseolous amino acid sequences presented herein. Methods of raising antibodies are well known in the art and are described in Harlow and Lane (1988). Such antibodies can then be used to screen an expression cDNA library produced from the plant from which it is desired to clone the zeatin O-glucosyltransferase or zeatin O-xylosyltransferase gene ortholog, using the methods described above. The selected cDNAs can be confirmed by sequencing and enzyme activity.

The disclosed Phaseolous sequences, and homologs of these sequences from other plants may be incorporated into transformation vectors and introduced into plants to modify zeatin O-glucosyltransferase activity and/or zeatin O-xylosyltransferase activity in such plants, as described in Example three below. It is anticipated that the native zeatin O-glucosyltransferase and/or zeatin O-xylosyltransferase gene promoter may be particularly useful in the practice of the present invention in that it may be used to drive the expression of zeatin O-glucosyltransferase and/or zeatin O-xylosyltransferase transgenes, such as antisense constructs. For example, by using the native zeatin O-glucosyltransferase gene promoter, expression of these transgenes may be regulated in coordination with the native zeatin O-glucosyltransferase gene (for example, in the same temporal or tissue-specific expression patterns).

Example Three

Transgenic Plants with Modified Zeatin O-glucosyltransferase and/or Zeatin O-xylosyltransferase Expression Once a gene (or cDNA) encoding a protein involved in the determination of a particular plant characteristic has been isolated, standard techniques may be used to express the cDNA in transgenic plants in order to modify that particular plant characteristic. The basic approach is to clone the cDNA into a transformation vector, such that it is operably linked to control sequences (e.g., a promoter) that direct expression of the cDNA in plant cells. The transformation vector is then introduced into plant cells by one of a number of techniques (e.g., electroporation) and progeny plants containing the introduced cDNA are selected. Preferably all or part of the transformation vector will stably integrate into the genome of the plant cell. That part of the transformation vector which integrates into the plant cell and which contains the introduced cDNA and associated sequences for controlling expression (the introduced "transgene") may be referred to as the recombinant expression cassette.

Selection of progeny plants containing the introduced transgene may be made based upon the detection of an altered phenotype. Such a phenotype may result directly from the cDNA cloned into the transformation vector or may be manifested as enhanced resistance to a chemical agent (such as an antibiotic) as a result of the inclusion of a dominant selectable marker gene incorporated into the transformation vector.

The choice of (a) control sequences and (b) how the cDNA (or selected portions of the cDNA) are arranged in the transformation vector relative to the control sequences determine, in part, how the plant characteristic affected by the introduced cDNA is modified. For example, the control sequences may be tissue specific, such that the cDNA is only expressed in particular tissues of the plant (e.g., pollen, seed) and so the affected characteristic will be modified only in those tissues. The cDNA sequence may be arranged relative to the control sequence such that the cDNA transcript is expressed normally, or in an antisense orientation. Expression of an antisense RNA corresponding to the cloned cDNA will result in a reduction of the targeted gene product (the targeted gene product being the protein encoded by the plant gene from which the introduced cDNA was derived). Overexpression of the introduced cDNA, resulting from a plus-sense orientation of the cDNA relative to the control sequences in the vector, may lead to an increase in the level of the gene product, or may result in co-suppression (also termed "sense suppression") of that gene product.

Successful examples of the modification of plant characteristics by transformation with cloned cDNA sequences are replete in the technical and scientific literature. Selected examples, which serve to illustrate the current knowledge in this field of technology, and which are herein incorporated by reference, include:

U.S. Pat. No. 5,451,514 to Boudet (modification of lignin synthesis using antisense RNA and co-suppression);

U.S. Pat. No. 5,443,974 to Hitz (modification of saturated and unsaturated fatty acid levels using antisense RNA and co-suppression);

U.S. Pat. No. 5,530,192 to Murase (modification of amino acid and fatty acid composition using antisense RNA);

U.S. Pat. No. 5,455,167 to Voelker (modification of medium chain fatty acids)

U.S. Pat. No. 5,231,020 to Jorgensen (modification of flavenoids using co-suppression);

U.S. Pat. No. 5,583,021 to Dougherty (modification of virus resistance by expression of plus-sense untranslatable RNA);

WO 96/13582 (modification of seed VLCFA composition using over expression, co-suppression and antisense RNA in conjunction with the Arabidopsis FAE1 gene); and WO 95/15387 (modification of seed VLCFA composition using over expression of jojoba wax synthesis gene).

These examples include descriptions of transformation vector selection, transformation techniques and the construction of constructs designed to over-express the introduced cDNA or to express antisense RNA corresponding to the cDNA. In light of the foregoing and the disclosed Phaseolous sequences, it is thus apparent that one of skill in the art will be able to introduce these nucleic acids, or homologous or derivative forms of these molecules (e.g., antisense forms), into plants in order to produce plants having modified zeatin O-glucosyltransferase activity and/or modified zeatin O-xylosyltransferase activity. Modification of the activity of zeatin O-glucosyltransferase and/or zeatin O-xylosyltransferase in plants will permit controlled modification of not only zeatin function, but also other cytokinins and, as a consequence of the interdependent regulation of plant hormones, other hormones. The result can be altered plant development with agricultural and economic consequences.

a. Plant Types

Zeatins are found in all plant types, and thus DNA molecules according to the present invention (e.g., the zeatin O-glucosyltransferase cDNA, the zeatin O-xylosyltransferase ORF, and the glucosyltransferase gene, homologs of these sequences and derivatives such as antisense forms) may be introduced into any plant type in order to modify the zeatin O-glucosyltransferase activity or the zeatin O-xylosyltransferase activity in the plant. Thus, the sequences of the present invention may be used to modify zeatin O-glucosyltransferase activity and/or zeatin O-xylosyltransferase activity in any higher plant, including monocotyledonous, dicotyledenous and gymnosperm plants, including, but not limited to maize, wheat, rice, barley, soybean, beans in general, rape/canola, alfalfa, flax, sunflower, safflower, brassica, pine trees such as the loblolly pine and Douglas fir, cotton, flax, peanut, clover; vegetables such as lettuce, tomato, cucurbits, potato, carrot, radish, pea, lentils, cabbage, broccoli, brussel sprouts, peppers; tree fruits such as apples, pears, peaches, apricots; flowers such as carnations and roses.

b. Vector Construction, Choice of Promoters

A number of recombinant vectors suitable for stable transfection of plant cells or for the establishment of transgenic plants have been described including those described in Pouwels et al., (1987), Weissbach and Weissbach, (1989), and Gelvin et al., (1990). Typically, plant transformation vectors include one or more cloned plant genes (or cDNAs) under the transcriptional control of 5' and 3' regulatory sequences and a dominant selectable marker. Such plant transformation vectors typically also contain a promoter regulatory region (e.g., a regulatory region controlling inducible or constitutive, environmentally-or developmentally-regulated, or cell- or tissue-specific expression), a transcription initiation start site, a ribosome binding site, an RNA processing signal, a transcription termination site, and/or a polyadenylation signal.

Examples of constitutive plant promoters which may be useful for expressing the cDNA include: the cauliflower mosaic virus (CaMV) 35S promoter, which confers constitutive, high-level expression in most plant tissues (see, e.g., Odel et al., 1985, Dekeyser et al., 1990, Terada and Shimamoto, 1990; Benfey and Chua. 1990); the nopaline synthase promoter (An et al., 1988); and the octopine synthase promoter (Fromm et al., 1989).

A variety of plant gene promoters that are regulated in response to environmental, hormonal, chemical, and/or developmental signals, also can be used for expression of the cDNA in plant cells, including promoters regulated by: (a) heat (Callis et al., 1988; Ainley, et al. 1993; Gilmartin et al. 1992); (b) light (e.g., the pea rbcS-3A promoter, Kuhlemeier et al., 1989, and the maize rbcS promoter, Schaffner and Sheen, 1991); (c) hormones, such as abscisic acid (Marcotte et al., 1989); (d) wounding (e.g., wun1, Siebertz et al., 1989); and (e) chemicals such as methyl jasminate or salicylic acid (see also Gatz et al., 1997) can also be used to regulate gene expression.

Alternatively, tissue specific (root, leaf, flower, and seed for example) promoters (Carpenter et al. 1992, Denis et al. 1993, Opperman et al. 1993, Stockhause et al. 1997; Roshal et al., 1987; Schernthaner et al., 1988; and Bustos et al., 1989) can be fused to the coding sequence to obtain particular expression in respective organs. In addition, the timing of the expression can be controlled by using promoters such as those acting at senescence (Gan and Amasino 1995) or late seed development (Odell et al. 1994).

The promoter region of the zeatin O-glucosyltransferase gene sequence disclosed herein (Shown in Seq. I.D. No. 6) confers seed-specific expression in *P. lunatus*. Accordingly, the native promoter may be used to obtain seed specific expression of the introduced transgene.

Plant transformation vectors may also include RNA processing signals, for example, introns, which may be positioned upstream or downstream of the ORF sequence in the transgene. In addition, the expression vectors may also include additional regulatory sequences from the 3'-untranslated region of plant genes, e.g., a 3' terminator region to increase mRNA stability of the mRNA, such as the PI-II terminator region of potato or the octopine or nopaline synthase 3' terminator regions.

Finally, as noted above, plant transformation vectors may also include dominant selectable marker genes to allow for the ready selection of transformants. Such genes include those encoding antibiotic resistance genes (e.g., resistance to hygromycin, kanamycin, bleomycin, G418, streptomycin or spectinomycin) and herbicide resistance genes (e.g., phosphinothricin acetyltransferase).

c. Arrangement of Zeatin O-glucosyltransferase and/or O-xylosyltransferase Sequence in Vector The particular arrangement of the zeatin O-glucosyltransferase sequence and/or zeatin O-xylosyltransferase sequence in the transformation vector will be selected according to the type of expression of the sequence that is desired.

Where enhanced zeatin O-glucosyltransferase activity and/or enhanced zeatin O-xylosyltransferase activity is desired in the plant, the zeatin O-glucosyltransferase ORF and/or the zeatin O-xylosyltransferase ORF may be operably linked to a constitutive high-level promoter such as the CaMV 35S promoter. As noted below, modification of zeatin O-glucosyltransferase synthesis and/or zeatin O-xylosyltransferase synthesis may also be achieved by introducing into a plant a transformation vector containing a variant form of the disclosed Phaseous sequences. For example, a form can vary from the exact nucleotide sequence of the zeatin O-glucosyltransferase ORF, but still encode a protein that retains the functional characteristic of the zeatin O-glucosyltransferase protein, i.e., O-glucosylation of cytokinins, such as zeatin.

In contrast, a reduction of zeatin O-glucosyltransferase activity and/or zeatin O-xylosyltransferase activity in the transgenic plant may be obtained in a number of different ways. For example, a reduction in protein product can be achieved through the use of antisense sequences, ribozymes, co-suppression, untranslatable RNAs, and/or dominant negative mutants.

For antisense suppression, the disclosed Phaseolous sequences are arranged in reverse orientation relative to the promoter sequence in the transformation vector. The introduced sequence need not be the full length of the disclosed Phaseolous sequences, and need not be exactly homologous to the endogenous zeatin O-glucosyltransferase or the endogenous zeatin O-xylosyltransferase found in the plant type to be transformed. Generally, however, where the introduced sequence is of shorter length, a higher degree of homology to the endogenous zeatin O-glucosyltransferase sequence and/or the endogenous zeatin O-xylosyltransferase sequence will be needed for effective antisense suppression. Preferably, the introduced antisense sequence in the vector will be at least 30 nucleotides in length, and improved antisense suppression will typically be observed as the length of the antisense sequence increases. Preferably, the length of the antisense sequence in the vector will be greater than 100 nucleotides. Transcription of an antisense construct as described results in the production of RNA molecules that are the reverse complement of mRNA molecules transcribed from the endogenous zeatin O-glucosyltransferase and/or zeatin O-xylosyltransferase gene(s) in the plant cell. Although the exact mechanism by which antisense RNA molecules interfere with gene expression has not been elucidated, it is believed that antisense RNA molecules bind to the endogenous mRNA molecules and thereby inhibit translation of the endogenous mRNA.

Suppression of endogenous zeatin O-glucosyltransferase and/or zeatin O-xylosyltransferase expression can also be achieved using ribozymes. Ribozymes are synthetic RNA molecules that possess highly specific endoribonuclease activity. The production and use of ribozymes are disclosed in U.S. Pat. No. 4,987,071 to Cech and U.S. Pat. No. 5,543,508 to Haselhoff. The inclusion of ribozyme sequences within antisense RNAs may be used to confer RNA cleaving activity on the antisense RNA, such that endogenous mRNA molecules that bind to the antisense RNA are cleaved, which in turn leads to an enhanced antisense inhibition of endogenous gene expression.

Constructs in which the disclosed Phaseolous sequences (or variants thereof) are over-expressed may also be used to obtain co-suppression of the endogenous zeatin O-glucosyltransferase and/or the endogenous zeatin O-xylosyltransferase in the manner described in U.S. Pat. No. 5,231,021 to Jorgensen. Such co-suppression (also termed sense suppression) does not require that the entire disclosed Phaseolous sequence be introduced into the plant cells, nor does it require that the introduced sequence be exactly identical to the endogenous zeatin O-glucosyltransferase sequence and/or the endogenous zeatin O-xylosyltransferase sequence. However, as with antisense suppression, the suppressive efficiency will be enhanced as (1) the introduced sequence is lengthened and (2) the sequence similarity between the introduced sequence and the endogenous zeatin O-glucosyltransferase gene and/or zeatin O-xylosyltransferase gene is increased.

Constructs expressing an untranslatable form of the zeatin O-glucosyltransferase mRNA and/or an untranslatable form of zeatin O-xylosyltransferase mRNA may also be used to suppress the expression of endogenous zeatin O-glucosyltransferase and/or endogenous zeatin O-xylosyltransferase. Methods for producing such constructs are described in U.S. Pat. No. 5,583,021 to Dougherty et al. Preferably, such constructs are made by introducing a premature stop codon into the zeatin O-glucosyltransferase ORF and/or the zeatin O-xylosyltransferase ORF.

Finally, dominant negative mutant forms of the disclosed Phaseolous proteins may be used to block endogenous zeatin O-glucosyltransferase activity or the endogenous zeatin O-xylosyltransferase activity. Such mutants require the production of mutated forms of the zeatin O-glucosyltransferase protein or the zeatin O-xylosyltransferase protein that bind to zeatin but do not catalyze the enzymatic step.

d. Transformation and Regeneration Techniques

Transformation and regeneration of both monocotyledonous and dicotyledonous plant cells is now routine, and the selection of the most appropriate transformation technique will be determined by the practitioner. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumeficiens* (AT) mediated transformation. Typical procedures for transforming and regenerating plants are described in the patent documents listed at the beginning of this section.

e. Selection of Transformed Plants

Following transformation and regeneration of plants with the transformation vector, transformed plants are preferably selected using a dominant selectable marker incorporated into the transformation vector. Typically, such a marker will confer antibiotic resistance on the seedlings of transformed plants, and selection of transformants can be accomplished by exposing the seedlings to appropriate concentrations of the antibiotic.

After transformed plants are selected and grown to maturity, they can be assayed using the methods described herein to determine whether zeatin O-glucosyltransferase activity and/or zeatin O-xylosyltransferase activity has been altered as a result of the introduced transgene. In addition, antisense or sense suppression of the endogenous zeatin O-glucosyltransferase and/or zeatin O-xylosyltransferase gene(s) may be detected by analyzing mRNA expression on Northern blots.

Example Four

Production of Sequence Variants

As noted above, modification of zeatin O-glucosyltransferase activity and/or zeatin O-xylosyltransferase activity in plant cells can be achieved by transforming plants with the disclosed Phaseolous sequences, antisense constructs based on the disclosed Phaseolous sequences, or other variants of the disclosed Phaseolous sequences. With the provision of the disclosed Phaseolous sequences herein, the creation of variants on these sequences by standard mutagenesis techniques is now enabled.

Variant DNA molecules include those created by standard DNA mutagenesis techniques, for example, M13 primer mutagenesis. Details of these techniques are provided in Sambrook et al. (1989), Ch. 15. By the use of such techniques, variants may be created which differ in minor ways from the disclosed Phaseolous sequences. DNA molecules and nucleotide sequences which are derivatives of those specifically disclosed herein and which differ from those disclosed by the deletion, addition or substitution of nucleotides while still encoding a protein which possesses the functional characteristic of the zeatin O-glucosyltransferase protein, or the functional characteristic of the zeatin O-xylosyltransferase protein (i.e., the ability to convert zeatin to O-glucosylzeatin or O-xylosylzeatin) are comprehended by this invention. DNA molecules and nucleotide sequences which are derived from the disclosed Phaseolous sequences include DNA sequences which hybridize under stringent conditions to the DNA sequences disclosed, or fragments thereof.

Hybridization conditions resulting in particular degrees of stringency will vary depending upon the nature of the hybridization method of choice and the composition and length of the hybridizing DNA used. Generally, the temperature of hybridization and the ionic strength (especially the $Na^+$ concentration) of the hybridization buffer will determine the stringency of hybridization. Calculations regarding hybridization conditions required for attaining particular degrees of stringency are discussed by Sambrook et al. (1989), chapters 9 and 11, herein incorporated by reference. By way of illustration only, a hybridization experiment may be performed by hybridization of a DNA molecule (for example, a variant of the Phaseolous zeatin O-glucosyltransferase cDNA sequence) to a target DNA molecule (for example, the Phaseolous zeatin O-glucosyltransferase cDNA sequence) which has been electrophoresed in an agarose gel and transferred to a nitrocellulose membrane by Southern blotting (Southern, 1975), a technique well known in the art and described in (Sambrook et al., 1989). Hybridization with a target probe labeled with $[^{32}P]$-dCTP is generally carried out in a solution of high ionic strength such as 6×SSC at a temperature that is 20–25° C. below the melting temperature, $T_m$, described below. For such Southern hybridization experiments where the target DNA molecule on the Southern blot contains 10 ng of DNA or more, hybridization is typically carried out for 6–8 hours using 1–2 ng/ml radiolabeled probe (of specific activity equal to $10^9$ CPM/μg or greater). Following hybridization, the nitrocellulose filter is washed to remove background hybridization. The washing conditions should be as stringent as possible to remove background hybridization but to retain a specific hybridization signal. The term $T_m$ represents the temperature above which, under the prevailing ionic conditions, the radiolabeled probe molecule will not hybridize to its target DNA molecule. The $T_m$ of such a hybrid molecule may be estimated from the following equation (Bolton and McCarthy, 1962):

$T_m$=81.5° C.−16.6($\log_{10}$[$Na^+$])+0.41(%$G+C$)−0.63(% formamide)−(600//)

Where /=the length of the hybrid in base pairs.

This equation is valid for concentrations of Na$^+$ in the range of 0.01 M to 0.4 M, and it is less accurate for calculations of $T_m$ in solutions of higher [Na$^+$]. The equation is also primarily valid for DNAs whose G+C content is in the range of 30% to 75%, and it applies to hybrids greater than 100 nucleotides in length (the behavior of oligonucleotide probes is described in detail in Ch. 11 of Sambrook et al., 1989).

Thus, by way of example, for a 150 base pair DNA probe derived from the first 150 base pairs of the open reading frame of the Phaseolous zeatin O-glucosyltransferase cDNA (with a hypothetical %GC=45%), a calculation of hybridization conditions required to give particular stringencies may be made as follows:

For this example, it is assumed that the filter will be washed in 0.3×SSC solution following hybridization, thereby [Na$^+$]=0.045M; %GC=45%; Formamide concentration=0; l=150 base pairs; and $T_m$=81.5° C.−16 (log$_{10}$[Na$^+$])+(0.41×45)−(600/150) and so $T_m$=74.4° C.

The $T_m$ of double-stranded DNA decreases by 1–1.5° C. with every 1% decrease in homology (Bonner et al., 1973). Therefore, for this given example, washing the filter in 0.333 SSC at 59.4–64.4° C. will produce a stringency of hybridization equivalent to 90%. Alternatively, washing the hybridized filter in 0.3×SSC at a temperature of 65.4–68.4° C. will yield a hybridization stringency of 94%. The above example is given entirely by way of theoretical illustration. One skilled in the art will appreciate that other hybridization techniques may be utilized and that variations in experimental conditions will necessitate alternative calculations for stringency.

DNA sequences from plants that encode a protein having zeatin O-glucosyltransferase activity and which hybridize under hybridization conditions of at least 75%, more preferably at least 80%, more preferably at least 85%, more preferably at least 90% and most preferably at least 95% stringency are encompassed within the present invention.

The degeneracy of the genetic code further widens the scope of the present invention as it enables major variations in the nucleotide sequence of a DNA molecule while maintaining the amino acid sequence of the encoded protein. For example, the second amino acid residue of the Phaseolous zeatin O-glucosyltransferase protein is alanine. This is encoded in the Phaseolous zeatin O-glucosyltransferase open reading frame by the nucleotide codon triplet GCT. Because of the degeneracy of the genetic code, three other nucleotide codon triplets—GCA, GCC and GCG—also code for alanine. Thus, the nucleotide sequence of the Phaseolous zeatin O-glucosyltransferase ORF could be changed at this position to any of these three codons without affecting the amino acid composition of the encoded protein or the characteristics of the protein. Based upon the degeneracy of the genetic code, variant DNA molecules may be derived from the cDNA and gene sequences disclosed herein using standard DNA mutagenesis techniques as described above, or by synthesis of DNA sequences. Thus, this invention also encompasses nucleic acid sequences which encode a zeatin O-glucosyltransferase protein but which vary from the disclosed nucleic acid sequences by virtue of the degeneracy of the genetic code.

One skilled in the art will recognize that DNA mutagenesis techniques may be used not only to produce variant DNA molecules, but will also facilitate the production of proteins which differ in certain structural aspects from the disclosed Phaseolous proteins, yet which proteins are clearly derivative of these proteins and which maintain the essential functional characteristics of zeatin O-glucosyltransferase or zeatin O-xylosyltransferase. Newly derived proteins may also be selected in order to obtain variations on the characteristics of the disclosed Phaseolous proteins, as will be more fully described below. Such derivatives include those with variations in amino acid sequence including minor deletions, additions and substitutions.

While the site for introducing an amino acid sequence variation is predetermined, the mutation per se need not be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence as described above are well known.

Amino acid substitutions are typically of single residues; insertions usually will be on the order of about from 1 to 10 amino acid residues; and deletions will range about from 1 to 30 residues. Deletions or insertions preferably are made in adjacent pairs, i.e., a deletion of 2 residues or insertion of 2 residues. Substitutions, deletions, insertions or any combination thereof may be combined to arrive at a final construct. Obviously, the mutations that are made in the DNA encoding the protein must not place the sequence out of reading frame and preferably will not create complementary regions that could produce secondary mRNA structure.

Substitutional variants are those in which at least one residue in the amino acid sequence has been removed and a different residue inserted in its place. Such substitutions generally are made in accordance with the following Table 3 when it is desired to finely modulate the characteristics of the protein. Table 3 shows amino acids which may be substituted for an original amino acid in a protein and which are regarded as conservative substitutions.

TABLE 3

Listing of Conservative Amino Acid Substitutions

| Original Residue | Conservative Substitutions |
|---|---|
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu, val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in enzymatic function or other features are made by selecting substitutions that are less conservative than those in Table 3, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The effects of these amino acid substitutions or deletions or additions may be assessed for derivatives of the zeatin O-glucosyltransferase protein and/or the zeatin O-xylosyltransferase protein by analyzing the ability of the derivative proteins to catalyze the conversion of zeatin to O-glucosylzeatin or zeatin to O-xylosylzeatin. These assays may conveniently be performed using the assay described above.

Example Five

Production of Recombinant Zeatin O-glucosyltransferase or Zeatin O-xylosyltransferase using Heterologous Expression Systems Many different expression systems are available for expressing cloned nucleic acid molecules. Examples of prokaryotic and eukaryotic expression systems that are routinely used in laboratories are described in Chapters 16–17 of Sambrook et al. (1989), which are herein incorporated by reference. Such systems may be used to express zeatin O-glucosyltransferase and/or zeatin O-xylosyltransferase at high levels to facilitate purification of the enzyme. The enzyme may be used for a variety of purposes. For example, it may be applied directly to plants to modulate zeatin function. Alternatively the purified enzyme produced by recombinant means may be used to synthesize O-glucosylzeatin, O-xylosylzeatin and other zeatin metabolites in vitro, particularly radio- or fluorescent-labeled forms of O-glucosylzeatin, O-xylosylzeatin and zeatin metabolites. These molecules may be used as tracers to determine the location in plant tissues and cells of zeatin and its metabolites. In addition, the recombinant form of the enzyme may be used to produce labeled forms of metabolites of other substrates (for example, isoprenylated proteins) on which it may act. The purified recombinant enzyme may also be used as an immunogen to raise enzyme-specific antibodies. Such antibodies are useful as both research reagents (such as in the study of zeatin regulation in plants) as well as diagnostically to determine expression levels of the enzyme in agricultural products, including seed.

By way of example only, high level expression of the zeatin O-glucosyltransferase-protein may be achieved by cloning and expressing the cDNA in yeast cells using the pYES2 yeast expression vector (Invitrogen, San Diego, Calif.). The recombinant zeatin O-glucosyltransferase may be supplied in the harvested yeast cells (for subsequent processing). Alternatively, a genetic construct may be produced to direct secretion of the recombinant zeatin O-glucosyltransferase from the yeast cells into the medium. This approach will facilitate the purification of the zeatin O-glucosyltransferase protein, if this is necessary. Secretion of the recombinant zeatin O-glucosyltransferase from the yeast cells may be achieved by placing a yeast signal sequence adjacent to the zeatin O-glucosyltransferase coding region. A number of yeast signal sequences have been characterized, including the signal sequence for yeast invertase. This sequence has been successfully used to direct the secretion of heterologous proteins from yeast cells, including such proteins as human interferon (Chang et al., 1986), human lactoferrin (Liang and Richardson, 1993) and prochymosin (Smith et al., 1985).

Alternatively, the enzyme may be expressed at high level in prokaryotic expression systems, such as *E. coli* as described above.

Example Six

Use of the Zeatin O-glucosyltransferase Gene Promoter Sequence

The promoter of the *Phaseolous lunatus* zeatin O-glucosyltransferase gene confers seed-specific expression. Accordingly, this promoter sequence, shown in Seq. I.D. No. 6, may be used to produce transgene constructs that are specifically expressed in seeds. One of skill in the art will recognize that effective seed-specific expression may be achieved with less than the entire 141 base pair sequence shown in Seq. I.D. No. 6. Thus, by way of example, seed-specific expression may be obtained by employing a 50 base pair or 100 base pair region of the disclosed promoter sequence. The determination of whether a particular sub-region of the disclosed sequence operates to confer effective seed-specific expression in a particular system (taking into account the plant species into which the construct is being introduced, the level of expression required, etc.) will be performed using known methods, such as operably linking the promoter sub-region to a marker gene (e.g. GUS), introducing such constructs into plants and then determining the level of expression of the marker gene in seeds and other plant tissues.

The present invention therefore facilitates the production, by standard molecular biology techniques, of nucleic acid molecules comprising this promoter sequence operably linked to a nucleic acid sequence, such as an open reading frame. Suitable open reading frames include open reading frames encoding any protein for which seed-specific expression is desired. Examples of genes that may suitably be expressed in a seed-specific manner under the control of the zeatin O-glucosyltransferase promoter include, but are not limited to:

(1) genes that enhance the nutritional quality of the seeds, for example, by increasing the content of limiting amino acids, including lysine, methionine and cysteine. This may be achieved by expressing proteins containing high levels of these amino acids in seeds. Examples include the high methionine storage proteins from brazil nut (Saalbach et al., 1996) and sunflower (Molvig et al., 1997).

(2) genes that increase gluten levels in wheat, so as to enhance the bread-making quality of the wheat flour (Shewry et al., 1995).

(3) genes that enhance insect resistance in the seed (for example, resistance to weevils). Suitable genes include the α-amylase inhibitor gene which kills seed weevils (Schmidt, 1994).

REFERENCES

Ainley et al. (1993) Regulatable endogenous production of cytokinins up to "toxic" levels in transgenic plants and plant tissues. *Plant Mol. Biol.* 22:13–23.

Altschul et al. (1990) Basic local alignment search tool. *J. Mol. Biol.* 215:403–410.

Altschul et al. (1994) *Nature Genet.*, 6, 119–29.

An et al. (1988) *Plant Physiol.* 88:547.

Ausubel et al. (1987) In *Current Protocols in Molecular Biology*, Greene Publishing Associates and Wiley-Intersciences.

Badenoch-Jones et al. (1996) Effect of cytokinins supplied via the xylem at multiples of endogenous concentrations on transcription and senescence in derooted seedlings of oat and wheat. *Plant Cell and Environment* 19:504–516.

Benfey & Chua (1990) The cauliflower mosaic virus 35S promoter: Combinatorial regulation of transcription in plants. *Science* 250:959–966.

Birch et al. (1997) Plant transformation: Problems and strategies for practical application. *Ann. Rev. Plant Physiol. Plant Mol. Biol.* 48:297–326.

Bolton & McCarthy (1962) *Proc. Natl. Acad. Sci. USA* 48:1390.

Bonner et al. (1973) *J. Mol. Biol.* 81:123.

Brzobohaty et al. (1993) Release of active cytokinin by a β-glucosidase localized to the maize root meristem. *Science* 262:1051–1054.

Bustos et al. (1989) *Plant Cell* 1:839.

Callis et al. (1988) *Plant Physiol.* 88:965.

Carpenter et al. (1992) Preferential expression of an α-tubulin gene of Arabidopsis in pollen. *The Plant Cell* 4:557–571.

Chang et al. (1986) *Saccharomyces cerevisiae* secretes and correctly processes human interferon hybrid protein containing yeast invertase signal peptides. *Mol. And Cell. Biol.* 6:1812–1819.

Corpet et al. (1988) *Nucleic Acids Research* 16, 10881–90.

Dekeyser et al. (1990) *Plant Cell* 2:591.

Denis et al. (1993) Expression of engineered nuclear male sterility in *Brassica napus*. *Plant Physiol.* 101:1295–1304.

Dixon et al. (1989) Zeatin glycosylation enzymes in Phaseolous. Isolation of O-glucosyltransferase from *P. lunatus* and comparison to O-xylosyltransferase from *P. vulgaris*. *Plant Physiology* 90:1316–1321.

Doyle & Doyle (1990) Isolation of plant DNA from fresh tissue. *Focus* 12:13–15.

Fromm et al. (1989) *Plant Cell* 1:977.

Gan & Amansino (1995) Inhibition of leaf senescence by autoregulated production of cytokinin. *Science* 270:1986–1988.

Gatz et al. (1997) Chemical control of gene expression. *Ann. Rev. Plant Physiol. Plant Mol. Biol.* 48:89–108.

Gelvin et al. (1990) *Plant Molecular Biology Manual*, Kluwer Academic Publishers.

Gilmartin et al. (1992) Characterization of a gene encoding a DNA binding protein with specificity for a light-responsive element. *The Plant Cell* 4:839–949.

Harlow & Lane (1988) *Antibodies, A Laboratory Manual*, Cold Spring Harbor Laboratory, N.Y.

Higgins & Sharp (1988) *Gene*, 73: 237–244.

Higgins & Sharp (1989) *CABIOS* 5: 151–153.

Hill et al. (1994) in *Selenium in Biology in Human Health*, ed. Burk, R. F. (Springer, N.Y.), pp. 117–132.

Hradecka & Petr (1992) The effect of cytokinins on the yield of some cereal plants. In: Physiology and Biochemistry of Cytokinins in Plants. Eds. Kaminek, M., D W S. Mok and E. Zazimalova. SPB Academic Publishing bv. 1992. pp. 245–247.

Huang et al. (1992) *Computer Applications in the Biosciences* 8, 155–65

Innis et al. (1990) *PCR Protocols, A Guide to Methods and Applications*, Innis et al. (eds.), Academic Press, Inc., San Diego, Calif.

Jameson (1994) Cytokinin metabolism and compartmentation. In: Cytokinins, Chemistry, Activity and Function. Eds. Mok, D W S and M C Mok. CRC Press. p.11 3–128.

Jorgensen et al. (1998) An RNA-based information super highway in plants. *Science* 279:1486–1487.

Karanov et al. (1992) Physiology and application of phenylurea cytokinins. In: Progress in Plant Growth Regulation (C. M. Karssen et al., eds.), pp. 842–851.

Kawasaki et al. (1990). In *PCR Protocols, A Guide to Methods and Applications*, Innis et al. (eds.), 21–27, Academic Press, Inc., San Diego, Calif.

Krikorian (1995) Hormones in tissue culture and micropropagation. In: Plant Hormones-Physiology, *Biochemistry and Molecular Biology*. 2nd Edition. Ed. Davies, P J. Kluwer Academic Publishers. pp. 774–796.

Kuhlemeier et al. (1989) *Plant Cell* 1: 471.

Letham (1963) Zeatin, a factor inducing cell division from *Zea mays*. *Life Sciences* 8:569–573.

Letham et al. (1976) O-Glucosylzeatin and related compounds—a new group of cytokinin metabolites. *Ann. Botany* 41:261–263.

Lewis, et al. (1996) Cytokinins and fruit development in the kiwifruit (*Actinidia deliciosa*).
II. Effects of reduced pollination and CPPU application. *Physiol. Plant.* 98:187–195.

Liang & Richardson (1993) Expression and characterization of human lactoferrin in yeast (*Saccharomyces cerevisiae*). *J. Agric. Food Chem.* 41:1800–1807.

Marcotte et al. (1989) *Plant Cell* 1:969.

Martin et al. (1990) Monoclonal antibody specific to zeatin O-glycosyltransferases of *Phaseolous, Plant Physiology* 94:1290–1294.

McGaw et al. (1983) Cytokinin oxidase from *Zea mays* kernels and Vinca rosea crown-gall tissue. *Planta* 159:30–37.

Meyer & Saedler (1996) Homology dependent gene silencing in plants. *Ann. Rev. Plant Physiol. Plant Mol. Biol.* 47:23–48.

Meyers & Miller (1988) *Computer Applic. Biol. Sci.*, 4: 11–17.

Miller et al. (1956) Isolation, structure and synthesis of kinetin, a substance promoting cell division. *Journal of American Chemical Society* 78:1375–1380.

Miller et al. (1955) Kinetin, a cell division factor from deoxyribonucleic acid. *Journal of American Chemical Society* 77:1392.

Minana et al. (1989) Endogenous cytokinins in developing fruits of seeded and seedless citrus cultivars. *J. Exp. Bot.* 219:1127–1134.

Mok & Martin (1994) Cytokinin metabolic enzymes. In: Cytokinins, Chemistry, Activity and Function. Eds. Mok, D W S and M C Mok. CRC Press. p.129–137.

Mok (1994) Cytokinins and plant development—An overview. In: Cytokinins, Chemistry, Activity and Function. Eds. Mok, D W S and M C Mok. CRC Press. p.155–166.

Molvig et al. (1997) Enhanced methionine levels and increased nutritive value of seeds of transgenic lupins (*Lupinus angustifolius L.*) expressing a sunflower seed albumin gene. *Proc. Natl. Acad. Sci.* 94:8393–8398.

Needleman & Wunsch (1970) *J. Mol. Biol.* 48: 443.

Newman et al. (1994) *Plant Physio.* 106: 1241–1255.

Ochman et al. (1989) Inverse polymerase chain reaction. In: PCR Technology-Principles and Applications for DNA Amplification. Ed. Erlich, HA. pp.105–111.

Odel et al. (1985) *Nature* 313:810.

Odell et al. (1994) Seed specific gene activation mediated by the Cre/lox site-specific recombination system. *Plant Physiol.* 106:447–458.

Opperman et al. (1993) Root knot nematode directed expression of a plant root specific gene. *Science* 263:221–223.

Pearson & Lipman (1988) *Proc. Natl. Acad. Sci. USA* 85: 2444.

Pearson et al. (1994) *Methods in Molecular Biology* 24, 307–31.

Pouwels et al. (1987) *Cloning Vectors: A Laboratory Manual*, 1985, supp.

Roshal et al. (1987). *EMBO J.* 6:1155.

Saalbach et al. (1996) The vacuolar targeting signal of the 2S albumin from Brazil nut resides at the C terminus and involves the C-terminal propeptide as an essential element. *Plant Physiol.* 112:975–985.

Saiki et al. (1989). *Proc. Nat Acad. Sci. USA* 86:6230–6234.

Sambrook et al. (1989) *In Molecular Cloning: A Laboratory Manual*, Cold Spring Harbor, N.Y.

Schaffner & Sheen (1991) *Plant Cell* 3:997.

Schernthaner et al. (1988) *EMBO J.* 7:1249.

Schmidt (1994) Genetic engineering yields. First pest resistant seeds. *Science* 265:739.

Shaw et al. (1964) A synthesis of zeatin. *Proceeedings of Chemical Society* 231.

Shaw (1994) Chemistry of adenine cytokinins. In: Cytokinins, Chemistry, Activity and Function. Eds. Mok, D W S and M C Mok. CRC Press. p.15–34.

Shewry et al. (1995) Seed storage proteins: structures and biosynthesis. *The Plant Cell* 7:945–956.

Siebertz et al. (1989) *Plant Cell* 1:961.

Skoog et al. (1965) Cytokinins. *Science* 148:532.

Smith et al. (1985) Heterologous protein secretion from yeast. *Science* 229:1219–1224.

Smith & Waterman (1981) *Adv. Appl. Math.* 2: 482.

Southern (1975). *J. Mol. Biol.* 98:503.

Southern et al. (1982) *J. Mol. Appl Genet.* 1:327–341.

Stockhause et al. (1997) The promoter of the gene encoding the $C_4$ form of phosphoenolpyruvate carboxylase directs mesophyll-specific expression in transgenic $C_4$ Flaveria spp. *The Plant Cell* 9:479–489.

Terada & Shimamoto (1990) *Mol. Gen. Genet.* 220:389.

Tijssen (1993) Laboratory Techniques in *Biochemistry and Molecular—Biology-Hybridization with Nucleic Acid Probes* Part I, Chapter 2 "Overview of principles of hybridization and the strategy of nucleic acid probe assays", Elsevier, N.Y.

Turner, J. E., Mok, D. W. S., Mok, M. C. and Shaw, G. 1987. Proceedings of National Academy of Sciences (USA). 84: 3714–717.

Weissbach & Weissbach (1989) Methods for Plant Molecular Biology, Academic Press.

Worley et al. (1995) BEAUTY: an enhanced BLAST-based search tool that integrates multiple biological information resources into sequence similarity search results. *Genome Research* 5:173–184.

---

We claim:

1. An isolated nucleic acid molecule encoding a polypeptide, the amino acid sequence of which comprises an amino acid sequence as set forth in SEQ ID NO: 4.

2. The nucleic acid molecule according to claim 1 comprising the sequence set forth as SEQ ID NO: 3.

3. An isolated nucleic acid molecule that encodes a polypeptide comprising an amino acid sequence selected from the group consisting of:
   (a) the sequence set forth in SEQ ID NO: 4; and
   (b) a sequence that shares at least 95% sequence identity with the sequence defined in (a), wherein the polypeptide has zeatin-O-glucosyltransferase activity.

4. A recombinant nucleic acid molecule comprising a promoter sequence operably linked to the nucleic acid molecule according to claim 1.

5. A recombinant nucleic acid molecule comprising a promoter sequence operably linked to the nucleic acid molecule according to claim 2.

6. A recombinant nucleic acid molecule comprising a promoter sequence operably linked to the nucleic acid molecule according to claim 3.

7. The recombinant nucleic acid molecule according to claim 5 wherein the nucleic acid molecule is in antisense orientation with respect to the promoter sequence.

8. A transgenic plant comprising the recombinant nucleic acid molecule according to claim 4.

9. A transgenic plant comprising the recombinant nucleic acid molecule according to claim 5.

10. A transgenic plant comprising the recombinant nucleic acid molecule according to claim 6.

11. A transgenic plant comprising the recombinant nucleic acid molecule according to claim 7.

* * * * *